United States Patent
Gorman et al.

(10) Patent No.: US 6,972,155 B2
(45) Date of Patent: Dec. 6, 2005

(54) GRADIENT FABRICATION TO DIRECT TRANSPORT ON A SURFACE

(75) Inventors: Christopher B. Gorman, Cary, NC (US); Daniel L. Feldheim, Cary, NC (US); Ryan R. Fuierer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/345,573

(22) Filed: Jan. 16, 2003

(65) Prior Publication Data

US 2003/0170480 A1  Sep. 11, 2003

Related U.S. Application Data

(60) Provisional application No. 60/349,906, filed on Jan. 18, 2002.

(51) Int. Cl.[7] .............................................. B32B 15/08
(52) U.S. Cl. ...................... 428/447; 428/450; 428/689; 428/701; 428/913; 427/256
(58) Field of Search ...................... 427/256; 428/689, 428/701, 913, 447, 450

(56) References Cited

U.S. PATENT DOCUMENTS

| | | | |
|---|---|---|---|
| 5,900,160 A | 5/1999 | Whitesides et al. | ........... 216/41 |
| 6,048,623 A | 4/2000 | Everhart et al. | ............ 428/464 |
| 6,132,685 A | 10/2000 | Kercso et al. | .............. 422/104 |
| 6,143,412 A | 11/2000 | Schueller et al. | ........... 428/408 |
| 6,180,239 B1 | 1/2001 | Whitesides et al. | ...... 428/411.1 |
| 6,228,248 B1 | 5/2001 | Aksay et al. | ............... 205/687 |
| 6,261,469 B1 | 7/2001 | Zakhidov et al. | ............. 216/56 |

FOREIGN PATENT DOCUMENTS

WO  WO 03/076082 A2 * 9/2003

OTHER PUBLICATIONS

Piner et al., "Dip-Pen" *Nanolithography*, Science 283:661663 (Jan. 29, 1999).
Xu et al., *Fabrication of Nanometer Scale Patterns within Self-Assembled Monolayes by Nanografting*, Langmuir 15: 7244-7251 (1999).

* cited by examiner

*Primary Examiner*—Marc S Zimmer
(74) *Attorney, Agent, or Firm*—Jenkins, Wilson & Taylor, P.A.

(57) ABSTRACT

The present invention discloses gradients and methods of forming gradients. The gradients can form a component of a molecular machine, such as those disclosed herein. The molecular machines of the present invention can perform a range of tasks including nanoparticle heterostructure assembly, derivatization of a nanoparticle and synthesis of biomolecules, to name just a few applications.

11 Claims, 17 Drawing Sheets

GRADIENT FABRICATION TO DIRECT TRANSPORT ON A SURFACE

CROSS REFERENCE TO RELATED APPLICATIONS

This application is based on and claims priority to U.S. provisional patent application Ser. No. 60/349,906, filed Jan. 18, 2002, herein incorporated by reference in its entirety.

TECHNICAL FIELD

The present invention relates to production of surface-bound chemical gradients. More specifically, the present invention relates to methods of employing surface-bound chemical gradients in a broad range of applications, including assembly of one-dimensional heterostructures and organic particle synthesis. The present invention also relates to methods of generating patterns on a surface.

Abbreviations

AFM—atomic force microscopy
CCD—charge coupled display
CdSe—cadmium selenide
$FcC_{11}SAc$—ferrocenyl-undecanethiol
IC—imaging conditions
ITO—indium tin oxide
LFM—lateral force microscopy
μm—micron
MEMS—microelectromechanical systems
MIM—metal-insulator-metal
MIS—metal-insulator-semiconductor
MS—metal-semiconductor
nm—nanometer
NSOM—near-field scanning optical microscopy
pA—picoampere
PDMS—poly(dimethylsiloxane)
$PK_a$—log of the acidity constant
RC—replacement conditions
RES—reticuloendothelial system
STM—scanning tunneling microscope
SAM—self-assembled monolayer
V—volt

BACKGROUND ART

Scanning probe lithography techniques can be employed to pattern self-assembled monolayers (SAMs) at the sub-micron length scale (Ross et al, (1993) *Langmuir* 9: 632; Schoer et al., (1996) *J. Phys. Chem.* 100: 11086; Zamborini & Crooks, (1998) *J. Am. Chem. Soc.* 120:9700; Xu & Liu, (1997) *Langmuir* 13: 127; Xu et al., (1998) *J. Am. Chem. Soc.* 120: 9356; Piner et al., (1999) *Science* 283: 661; Hong et al., (1999) *Science* 286: 523; Gorman et al., (2000) *Langmuir* 16: 6312; Xu et al., (1999) *Langmuir* 15: 7244; Maoz et al., (1999) *Adv. Mater.* 11: 55; Maoz et al., (2000) *Adv. Mater.* 12: 424). For example, Crooks and co-workers produced patterns in SAMs on gold by selectively removing the alkanethiolates with a scanning tunneling microscope (STM) (Ross et al, (1993) *Langmuir* 9:632; Schoer et al., (1996) *J. Phys. Chem.* 100:11086; Zamborini & Crooks, (1998) *J. Am. Chem. Soc.* 120: 9700). Recently, other SAM patterning techniques such as nanografting (Xu & Liu, (1997) *Langmuir* 13: 127; Xu et al., (1998) *J. Am. Chem. Soc.* 120: 9356), and dip pen nanolithography (Piner et al., (1999) *Science* 283: 661; Hong et al., (1999) *Science* 286: 523) have been described. More recently, an STM based replacement lithography technique was disclosed, in which SAM thiolates are selectively desorbed from the gold substrate and replaced with a second alkanethiol in solution (Gorman et al., (2000) *Langmuir* 16: 6312).

Chemical gradients transport materials in a directional manner, and are responsible for driving many important biological and physical processes. For example, the growth of axons from ganglions to target tissues and the directed movement of certain bacteria toward nutrients occur in response to concentration gradients of molecules emanating from axon target or food source (chemotaxis) (Ruardy et al., (1997) *Surf. Sci. Rep.* 29: 1). Concentration gradients of molecules in fluids or on surfaces also affect a variety of phenomena including osmotic swelling, surface pressure, and surface wettability. Efforts to establish and manipulate these parameters are ongoing in the art, as are efforts to develop new methods of transporting fluids in microchannels and new transport paradigms for the fabrication of chip-based chemical devices (Gallardo et al., (1999) *Science* 283: 57).

Surface-bound chemical gradients have previously been produced on millimeter to micron length scales (Ruardy et al., (1997) *Surf. Sci. Rep.* 29: 1; Gallardo et al., (1999) *Science* 283: 57; Chaudhury and Whitesides, (1992) *Science* 256: 1539; Daniel et al., (2001) *Science* 291: 633; Liedberg and Tengvall, (1995) *Langmuir* 11: 3821; Liedberg et al., (1997) *Langmuir* 13: 5329; Lestelius et al., (1999) *Colloid Surface B* 15: 57; Terrill et al., (2000) *J. Am. Chem. Soc.* 122: 988). In some cases, these gradients have been employed in directional transport. For example, Whitesides et al. fabricated SAM gradients consisting of decyltrichlorosilane on silicon substrates using a diffusion controlled vapor deposition technique. Water droplets were observed to travel uphill under the influence of the resulting spatial gradient in the surface free energy (Chaudhury and Whitesides, (1992) *Science* 256:1539). Liedberg et al. prepared millimeter scale SAM gradients on gold surfaces by cross-diffusing two different alkanethiols from opposite ends of a polysaccharide matrix (Liedberg and Tencivall, (1995) *Langmuir* 11: 3821; Liedberg et al., (1997) *Langmuir* 13: 5329; Lestelius et al., (1999) *Colloid Surface B* 15: 57).

None of the described studies, however, have employed STM-based replacement lithography to fabricate a surface-bound static or dynamic gradient. Moreover, prior to the present disclosure, the concept of static and dynamic gradients has not found application in the field of molecular machines. The ability to fabricate a surface-bound chemical gradient is desirable and can be employed in a range of applications. For example, a gradient so formed can be employed to construct a molecular machine, such as a particle synthesizer, as well as another machines and devices. STM-based gradient fabrication methods are also desirable, due to the relative availability of STM apparatuses that can be employed in the fabrication of gradients, as well as in the fabrication of other components of a molecular machine. To date, neither a static nor a dynamic STM-generated gradient on a nano- or micro-scale has been disclosed, nor has a gradient prepared in this fashion been disclosed as a component of a molecular machine. The present invention solves these and other problems.

SUMMARY OF THE INVENTION

A gradient disposed on a surface adapted to transport a fluid or a non-fluid is disclosed. In one embodiment, the gradient comprises: a surface; and a self-assembled monolayer (SAM) disposed on the surface, the SAM comprising a patterning material, the patterning material being disposed on the surface so as to define: (i) a first region defining an area of high driving force with respect to an interaction with a material to be transported; (ii) a second region defining an area of low driving force with respect to an interaction with a material to be transported; and (iii) a third region defining a region of diffuse driving force with respect to an interaction with a material to be transported, the third region being contiguous with the first and second regions.

In another embodiment, a gradient adapted to transport a fluid or a non-fluid is provided. The gradient comprises: a surface; and a self-assembled monolayer (SAM) disposed on the surface, the SAM comprising a patterning material that is adapted to vary in driving force in response to a stimulus.

A method of making a gradient on a surface is also disclosed. In one embodiment, the method comprises disposing a self-assembled monolayer (SAM) on a surface; and distributing a patterning material in the SAM, the patterning material defining a gradient on the surface.

In another aspect of the present invention, a method of making a gradient on a surface by microcontact printing is disclosed. In one embodiment, the method comprises: (a) providing a surface; (b) providing an application component; (c) contacting the application component with a patterning material to form a coated application component; (d) sequentially and continuously contacting the coated application component with contiguous regions of the surface until the patterning material is transferred from the application component to the surface.

In yet another aspect of the present invention, a method of making a gradient on a surface by vapor diffusion is disclosed. In one embodiment, the method comprises: (a) providing a surface maintained at a set of one or more conditions selected from the group consisting of pressure, pH, temperature and combinations thereof; (b) positioning a plug comprising a volatile patterning material proximate to the surface; and (c) varying the one or more conditions to thereby deposit variable concentrations of the patterning material at different points on the surface.

A method of forming a gradient on a surface is disclosed. In one embodiment, the method comprises: (a) providing a surface comprising a monolayer; (b) positioning an scanning tunneling microscope tip disposed in a solvent comprising a patterning material above the monolayer; and (c) rastering the scanning tunneling microscope tip in a desired pattern of lines while varying one or more of the surface-tip bias, the scan rate and the spacing between lines.

A molecular machine for assembling a nanoparticle heterostructure is disclosed. In one embodiment, the molecular machine comprises: (a) two or more reservoirs, each reservoir comprising a quantity of nanoparticles; (b) a reaction region; (c) two or more independently operable gate structures in communication with the two or more reservoirs and the reaction region; and (d) two or more dynamic gradient tracks, each in communication with an independently operable gate structure and the reaction region, the two or more dynamic gradient tracks comprising one or more regions of variable driving force. A method of assembling a one-dimensional nanoparticle heterostructure employing the disclosed molecular machine is also disclosed and, in one embodiment, comprises: (a) providing nanoparticles to the one or more reservoirs; (b) opening a first independently operable gate structure, thereby releasing a first nanoparticle; (c) varying the driving force of a first dynamic track, thereby directing the first nanoparticle down the first dynamic track to the reaction region; (d) closing the first independently operable gate structure and opening a second independently operable gate structure, thereby releasing a second nanoparticle; (e) varying the driving force of a second dynamic track, thereby directing the second nanoparticle down the second track to the reaction region and closing the second independently operable gate structure; and (f) repeating steps (a) through (e) a desired number of times.

A molecular machine for assembling a particle is also disclosed. In one embodiment, the molecular machine comprises: (a) two or more reservoirs comprising reaction components; (b) two or more independently operable gate structures in communication with the two or more reservoirs of components; (c) a reactor zone wherein a particle is assembled; (d) two or more static gradient tracks, each static gradient track communicating with one of the two or more independently operable gate structures and the reactor zone, the two or more static gradient tracks comprising fixed regions of high and low driving force; (e) an output track comprising a static gradient directing an assembled particle away from the reactor zone; and (f) an independently operable gate structure in communication with the output track and the reactor zone. A method of making a particle by employing the disclosed molecular machine is also disclosed and, in one embodiment, comprises: (a) providing reaction components to the one or more reaction component reservoirs; (b) opening a first independently operable gate structure, thereby releasing a first nanoparticle; (c) varying the driving force of a first static gradient track, thereby directing the first nanoparticle down the first static gradient track to the reactor zone; (d) closing the first independently operable gate structure and opening a second independently operable gate, thereby releasing a second nanoparticle; (e) varying the driving force of a second static gradient track, thereby directing the second nanoparticle down the second static gradient track to the reactor zone and closing the second independently operable gate structure; and (f) repeating steps (a) through (e) a desired number of times.

Additionally, a molecular machine for synthesizing a structure is disclosed. In one embodiment, the molecular machine comprises: (a) a reservoir comprising a starting material; (b) two or more reaction sites; (c) two or more dynamic gradient tracks, each in communication with the two or more reaction sites, the two or more dynamic gradient tracks comprising regions of variable driving force and each reaction site comprising a reaction component; (d) an output track comprising a dynamic gradient track comprising a region of variable driving force and adapted to direct a completed structure away from a reaction site; and (e) an independently operable gate structure in communication with the output track. A method of making a particle by employing the disclosed molecular machine is also disclosed and, in one embodiment, the method comprises: (a) providing a starting material; (b) transporting the starting material to a reaction site comprising a reaction component; (c) performing a chemical reaction on the starting material comprising associating a reaction component with the starting material to form an intermediate structure; (d) transporting the intermediate structure to a reaction site distinct from the first reaction site, the distinct site comprising a reaction component; (e) repeating steps (a) through (d) a desired number of times to form a completed structure; and (f) directing the completed structure down the output track.

Accordingly, it is an object of the present invention to provide a novel gradient disposed on a surface. This and other objects are achieved in whole or in part by the present invention.

Some of the objects of the invention having been stated hereinabove, other objects will be evident as the description proceeds, when taken in connection with the accompanying drawings as best described hereinbelow.

BRIEF DESCRIPTION OF THE DRAWINGS

FIG. 5A is not to scale and is presented schematically to illustrate the apparatus and method of microcontact printing aspect of the present invention.

DETAILED DESCRIPTION OF THE INVENTION

Figure 1A:
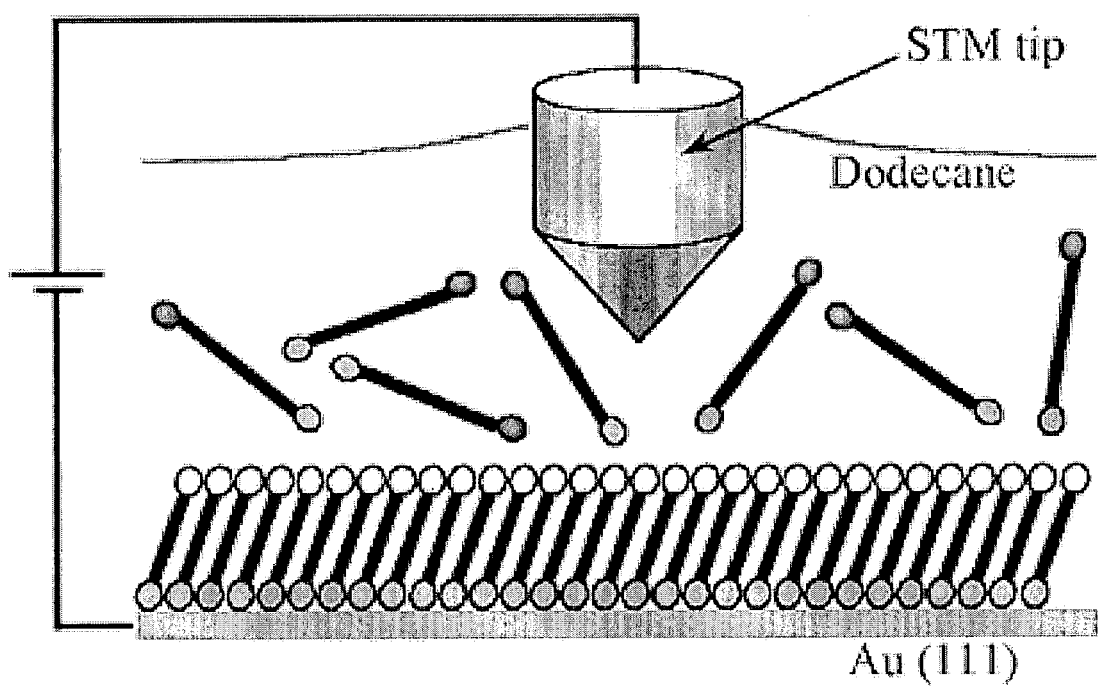
FIG. 1A is a schematic diagram depicting the motion of an STM tip over a SAM. The tip is disposed in a solution comprising dodecane and a replacement material.

The present invention discloses gradients and molecular machines adapted to perform a range of tasks, including derivatization of particles and synthesis of biomolecules and organic molecules. The gradients of the present invention can be dynamic or static, and can comprise an element of the molecular machines of the present invention. Methods of forming gradients, such as nanolithographic and microcontact printing methods, comprise an aspect of the present invention.

I. Definitions

Following long-standing patent law convention, the terms "a" and "an" refer to "one or more" when used in this application, including the claims.

As used herein, the terms "amino acid," "amino acid residue," and "residue" refer to an amino acid formed upon chemical digestion (hydrolysis) of a peptide or polypeptide at its peptide linkages. Amino acids can also be synthesized individually or as components of a peptide. The amino acid residues described herein are in one embodiment in the "L" isomeric form. However, residues in the "D" isomeric form can be substituted for any L-amino acid residue, as long as the desired functional property is retained by the polypeptide. In the context of an amino acid, $NH_2$ refers to the free amino group present at the amino terminus of a polypeptide, although some amino acids can have $NH_2$ groups at other positions in the amino acid. COOH refers to the free carboxy group present at the carboxy terminus of a polypeptide.

It is noted that amino acid residue sequences represented herein by formulae have a left-to-right orientation in the conventional direction of amino terminus to carboxy terminus. In addition, the terms "amino acid," "amino acid residue," and "residue" are broadly defined to include the 20 fundamental amino acids and modified or unusual amino acids.

As used herein, the term "application component" refers to any structure adapted to transfer a material disposed on the structure to a surface. An application component can comprise any composition or geometric configuration that is chemically compatible with a material to be transferred.

As used herein, the term "driving force" broadly refers to any force or impetus tending to direct a particle or molecule in a given direction or at a given rate of movement. A driving force can be affected by the application of a stimulus, such as a change in pH. In the present invention, for example, a driving force can be applied by a gradient and can direct a particle or molecule in contact with the gradient at a first position to a second position on the gradient. Such a driving force can arise from any of a variety of physical properties, such as the inherent nature of a hydrophobic molecule or particle disposed on a hydrophilic surface to move toward an area of low hydrophilicity and therefore, higher hydrophobicity. In another embodiment, a driving force can arise from the inherent nature of a positively charged species disposed in a region of positive charge to move to an area of a higher degree of negative charge, and therefore, a region of lower positive charge.

As used herein, the term "dynamic gradient" refers to a gradient that is variable in direction or slope of change in the concentration of a given chemical functionality (e.g., how quickly a surface composition changes from 100% of a first component to 100% of a second component). That is, a dynamic gradient comprises a gradient, as that term is defined herein, that is adapted to transfer a molecule or particle associated with the gradient in more than one direction. Unlike a static gradient, the properties and behavior of a dynamic gradient can be altered by applying a stimulus, such as an alteration in the pH, in the local environment of the gradient.

As used herein, the term "electroactive" refers to having the ability to change electronic configuration. The term refers to a molecule or structure and includes the ability to transfer electrons, the ability to act as a conductor of electrons and/or the ability to act as an electron donor or acceptor.

As used herein, the term "gold" refers to element 79, which has the chemical symbol Au; the term specifically excludes any connotation related to color or other calorimetric properties.

As used herein, the term "gradient" refers to a graduated difference in a property (e.g., potential energy or chemical composition) in a given direction from a given reference point.

As used herein, the term "gradient material" refers to any material that forms a component of a gradient. In one embodiment, a gradient material comprises a binding group, such as a thiolate group that facilitates association of the gradient material with a surface, and a head group, such as an acidic functional group, with which a particle in contact with a gradient will interact.

As used herein, the term "independently operable gate structure" refers to a structure that can adopt a state of open, partially open, or closed in response to a stimulus. A stimulus can comprise, for example, an electrical current, a change in pH, the presence or absence of a stimulating molecule or a change in the local electrostatic environment of the independently operable gate structure. The status of an "independently operable gate structure" as open, partially open or close is independent of the status of any other gate structures in the area surrounding the independently operable gate structure.

As used herein, the term "matrix material" refers to any material that forms a component of a monolayer (e.g., a SAM). In the present invention, a matrix material comprises in one embodiment a binding group that facilitates association of the matrix material with a surface and a functional group that forms an exposed face of the monolayer and is distal to the binding group. The term "matrix material" can refer to a three-dimensional structure, but need not do so. Indeed, in one embodiment, a matrix material forms a coherent formation that is one molecule thick.

The term "microparticle" as used herein denotes a structure that has a longest dimension of about 1000 $\mu$m or less. Thus, microparticles can be solid particles ranging in size from about 1 to 1000 $\mu$m. A microparticle can have any diameter less than or equal to 1000 $\mu$m including, but not limited to 1, 2, 3, 4, 5, 10, 15, 20, 25, 30, 50, 100, 500 and 750 $\mu$m. Drugs, bioactive material, organic compounds, functional groups, and other relevant materials can be incubated with the microparticles, and thereby be adsorbed or attached to the microparticle.

As used herein, the term "molecular machine" refers to any device that can perform work, and comprises in one embodiment one or more elements having nano- or microscale dimensions. Additionally, the term encompasses a device that performs an operation on a molecule or nanoparticle, such as the association of a molecule or other chemical moiety with the molecule or nanoparticle.

As used herein, the term "molecule" takes it understood meaning. The term "molecule" also encompasses macromolecules such as antibodies, peptides, proteins, and fragments thereof. Nucleic acids of all sizes are also encompassed by the term.

As used herein, the terms "nano", "nanoscopic" "nanometer-sized", "nanostructured", "nanoscale", "nanoparticle complexes" and grammatical derivatives thereof are used synonymously and interchangeably and refer to nanoparticles, nanoparticle composites, and hollow nanocapsules in one embodiment less than or equal to about 1000 nanometers (nm) in diameter, in another embodiment less than about 30 nanometers in diameter, and in still another embodiment less than about 10 nanometers in diameter. A nanoparticle can be fashioned from any material. In one embodiment, a nanoparticle is fashioned of a semiconductor material or metal, and in another embodiment of gold, $TiO_2$, or gold or $TiO_2$-containing materials. In still another embodiment, a nanoparticle is fashioned of biodegradable materials. The terms can refer not only to the metal component of a nanoparticle, but the composite of metal and other component parts as well.

The term "nanoparticle" as used herein denotes a structure that has a longest dimension of about 1000 nm or less. Thus, nanoparticles can be solid particles ranging in size from about 1 to 1000 nm. A nanoparticle can have any diameter less than or equal to 1000 nm, including, but not limited to 1, 2, 3, 4, 5, 10, 15, 20, 25, 30, 50, 100, 500 and 750 nm. Drugs, bioactive material, organic compounds, functional groups and other relevant materials can be incubated with the nanoparticles, and thereby be adsorbed or attached to the nanoparticle.

As used herein, the term "patterning material" refers to any material that is substituted for a matrix or other material desorbed from a surface. Exemplary patterning materials comprise a binding group, such as a thiolate group, that facilitates association of the gradient material with a surface, and a head group, such as an acidic functional group, with which a particle in contact with a gradient will interact.

As used herein, the terms "redox compound", "redox center", "redox group" and "redox active group" are used interchangeably and refer to a molecule or part of a molecule that is able to undergo changes in its electronic properties.

As used herein, the terms "self assembled monolayer", "SAM", and "monolayer" are used interchangeably and refer to a structure comprising a population of one or more distinct chemical entities which associate with one another to form a coherent formation that is one molecule thick.

As used herein, the term "static gradient" refers to a gradient that is unalterably oriented in one direction. That is, a static gradient comprises a gradient that is adapted to transfer a molecule or particle associated with the gradient in only one direction. Unlike a dynamic gradient, the properties and/or behavior of a static gradient cannot be altered by applying a stimulus.

As used herein, the term "stimulating molecule" refers to a molecule that possesses the ability to alter the behavior of a gate structure of the present invention. A stimulating molecule can affect the rate and/or amount of a particle or molecule able to pass through a gate structure positively or negatively. For example, a stimulating molecule can make a gate structure more "open" and thus permit a greater rate and/or amount of a particle or molecule to pass through the gate. Alternatively, a stimulating molecule can make a gate structure more "closed" and thus inhibit the passage of a particle and/or a molecule through the gate.

As used herein, the term "thiol" refers to a sulfur-containing organic compound with the general formula RSH, where R is any organic structure.

As used herein, the term "thiolate" and "thiolate ion" are used interchangeably and refer to a thiol salt, which can be produced from a corresponding thiol by abstraction of a proton via a base.

As used herein, the term "transported molecule or particle" refers to a molecule or particle that is, was, or is intended to be transported along a gradient of the present invention.

II. General Considerations for Scanning Tunneling Microscopy

Some of the methods of the present invention rely, in part, on employing a scanning tunneling microscope (STM). For example, a scanning tunneling microscope (STM) system comprising an STM tip can be employed to desorb matrix material from a monolayer (e.g. a SAM) in a desired location and thereby form a pattern.

The scanning tunneling microscope was originally developed for observing the surface structure of a solid sample at the atomic level. In STM operation, a sharp pointed probe is brought to within a distance of about 1 nm from the sample surface and a predetermined bias voltage is applied between the sample and the probe. As a result of this configuration, a tunneling current flows between them. The intensity of the tunneling current is very sensitive to the distance between the sample and the probe. The probe is scanned over the sample surface in parallel with the sample surface by being controlled up and down in a direction perpendicular to the sample surface for keeping the intensity of the tunnel current at a predetermined value. By doing this, the unevenness of the sample surface can be observed by the trail of the probe. As noted, scanning tunneling microscopy systems were developed to employ electron tunneling for structural and spectroscopic imaging of the surfaces of samples.

In practice, electron tunneling occurs when a voltage is placed across two conductors separated by a sufficiently thin insulating layer. In STM systems, the first conductor is the tip of the STM system and the second conductor is the sample whose surface is to be imaged. The insulating layer can be a liquid layer or a vacuum between the STM tip and surface of the sample. The current between the conductors (resulting from the voltage across them and the insulating layer) is a function of the conductor or electrode separation and the nature of the electronic states of the tip and sample.

To perform structural imaging in STM systems, the tunneling current between the tip and sample is measured while scanning the tip across the surface of the sample in, for example, a raster pattern. If the distance between the sample and the tip is adjusted to keep the current constant, a plot of the tip-sample distance versus position of the tip provides an indication of the structure of the surface of the sample. To perform spectroscopic imaging, the position of the tip over the sample is fixed for a period of time while the voltage across the tip and sample is varied. A plot of the deviation of the tunneling current against voltage for different positions of the tip enables the spectroscopic imaging of the surface of the sample.

STM has found application in fields distinct from microscopy. For example, STM lithography employing a scanning tunneling microscope (STM) has been employed to generate patterns on a surface (Ross et al., (1993) *Langmuir* 9: 632; Schoer et al., (1996) *J. Phys. Chem.* 100: 11086; Zamborini & Crooks, (1998) *J. Am. Chem. Soc.* 120: 9700). In STM lithography, atoms or molecules can be adsorbed onto or removed from a substrate with the resolving power determined, in part, by the shape of the tip of a probe. See e.g, Shedd et al., (1990) *Nanotechnology* 1: 67–80.

In this application, a voltage is applied between a probe (also referred to throughout the present disclosure as an STM tip) and a surface, generating a tunneling current or a field-emitted current between the probe and the surface. The tunneling current takes the form of an electron beam having a diameter determined, in part, by the shape of the probe tip. The diameter can be reduced to as small as about 1 nm. By directing a gas comprising atoms or molecules onto the substrate while simultaneously applying the tunneling current (electron beam) between the probe and the substrate, the atoms or molecules can be adsorbed onto only that portion of a substrate on which the tunneling current flows, a situation schematically depicted in FIGS. 1A–1C and FIGS. 8A–8C. That is, a desired amount of atoms or molecules can be deposited on the surface, with the resolving power of the electron beam determined by the diameter thereof. Further, molecules or atoms comprising a thin film (i.e., a monolayer) formed on a substrate can be desorbed by varying the above conditions. Also in this case, desorption is performed only in the portion on which the tunneling current (electron beam) flows, so that the thin film is etched with the resolving power of the beam as determined by the diameter thereof. Thus, an ultra fine pattern is formed, which cannot be formed by employing photolithography and other related methods known in the art.

III. Molecular Machines

The status of molecular machine research is still in the formative stages, and the present disclosure adds to the development of this field. Generally, several elements can be present in a machine. A machine comprises in one embodiment organized components that facilitate constrained, productive motion (i.e., work). A machine has in one embodiment a definable input, a definable process, and a definable output. The energy consumed per unit of work done constitutes efficiency. Additionally, in one embodiment a machine has a directionality associated with it; that is, there is some spatiotemporal path defining the operation of the machine.

In one aspect of the present invention, directionality at the molecular scale is disclosed and, via this directionality, nanometer and micrometer-scale operations and syntheses can be performed. The general approach of one aspect of the present invention is to guide functional particles along a defined pattern by employing controlled, reversible, non-covalent interactions. A pattern can comprise a gradient (e.g., a chemical gradient, an electrical gradient, a biochemical gradient, etc.) to stimulate motion (i.e., apply a driving force) and to define the direction of motion. These gradients can comprise a static gradient or a dynamic gradient.

Non-covalent guidance also plays a role in the present invention; some interaction is preferable so that the machine is constrained. Constraining non-covalent forces are reversible and weak enough that these forces can be overcome and motion relative to a non-covalent driving force-imparting moiety can be achieved. It is this concept of constrained motion that is a basic characteristic of a machine. In the context of the present invention, patterns can define the shape of the machine and, in one aspect, reduce the problem of manufacturing to one dimension, permitting the operation of a "molecular assembly line."

The present invention is not an extension of microfluidics and is, in fact, not fluidics at all since there is no bulk flow. In the present invention, transport characteristics are not defined by Reynolds numbers, as is characteristic of a fluid-based system. As disclosed herein below, the transport accomplished by the methods and apparatuses of the present invention can occur via specific, non-covalent interactions. This approach is uniquely suited to transportation of particles and reaction components on a molecular scale. However, this approach is also scaleable to larger sizes, and the present invention is not limited to molecular-scale transport and operations. Furthermore, the general nature of the transport mechanisms disclosed in the present invention is substantially more controlled and controllable as compared to other transport mechanisms, such as laminar flow-based mechanisms. In the present invention, for example, transport of a molecule or a particle can be highly nonlinear when employing the methods of the present invention (e.g., elements can be maintained at a given location and/or be redirected to another location). This level of control does not exist in the methods and apparatuses currently existing in the art.

The apparatuses and methods of the present invention also bear little resemblance to the type of "molecular machines" typically described in the art. Notably, traditional molecular machines move, but this is generally all that they do. All molecules have some minimal dynamic behavior (e.g., chair-half chair-boat-twist boat conformation interconversion of cyclohexane). However, dynamics that are not harnessed are not useful. Additionally, motion in traditional molecular machines is typically not directional, which severely limits the utility of these prior art machines. To the extent that traditional approaches define direction, it is not clear how they could be made to produce an effect on an input.

In order to achieve functionality, the present invention expands the paradigm for construction of molecular machines beyond the synthesis of chemically discrete molecules. Chemical synthesis is a powerful construction technique; however, its exclusive use can be limiting. Synthesis can be laborious, and often it is not modular and is not scalable past a 10 nm size limit. The present invention solves these and other problems.

Thus, the present invention expands the term "synthesis" to include the concepts of nano- and microscale fabrication. In the present invention, then, the term "molecular machine" encompasses harnessing chemically specific interactions that can be used to drive a process (e.g., perform work). The molecular machines and related methods of the present invention, therefore, are designed to be modular and can be applied in a future molecular machine, as new machines are developed, without a loss of functionality. Moreover, fabrication and operation of the molecular machines of the present invention can be done at any length scale, from the nanometer and micrometer scales up to even the centimeter scale.

IV. Crafting a Patterned Surface

A well-known method of producing devices, especially in the area of microelectronics, is photolithography. According to this technique, a negative or positive resist (photoresist) is coated onto an exposed surface of an article. The resist then is irradiated in a predetermined pattern, and portions of the resist that are irradiated (positive resist) or nonirradiated (negative resist) are removed from the surface to produce a predetermined pattern of resist on the surface. In addition to photolithography, x-ray and electron-beam lithography have found analogous use. Lithography techniques such as these are relatively labor intensive. Furthermore, these techniques can require the design and fabrication of chrome masks, access to clean rooms, and specialized equipment along with other considerations that often make these techniques impractical. The methods of the present invention do not suffer from these problems.

A well-known goal of photolithography is in the preparation of semiconductor circuitry. Various forms of lithography have been employed in the preparation of circuitry and in a range of other applications as well. However, lithographic methods have seen only limited use in preparing chemical "etchings" and, to date, have never been employed in the fabrication of molecular machines. This and other applications form aspects of the present invention and are discussed herein below.

IV.A. Preparation of a Self-Assembled Monolayer (SAM)

Self-assembled monolayers (SAMs) have been described in the art. See, e.g., Dubois et al., (1992) *Annu. Rev. Phys. Chem.* 43: 437, which is incorporated herein by reference. Recently, one class of SAMs that has received considerable attention is organomercaptans. See, e.g., Porter et al., (1987) *J. Am. Chem. Soc.* 109, 3559–3568; Bain & Whitesides, (1988) *J. Am. Chem. Soc.* 110, 3665–3666; Bain & Whitesides, (1988) *Science* 240, 62–63; Bain et al., (1989) *J. Am. Chem. Soc.* 111, 321–335, each of which is incorporated herein by reference in its entirety.

In one embodiment, a SAM comprising a matrix material is disposed on a surface. If a homogeneous monolayer is desired, a matrix material can comprise a single chemical species. If a heterogeneous monolayer is desired, a matrix material can comprise two or more chemical species. When formed, a monolayer is one molecule thick, although the dimensions of the monolayer can vary with the chemical composition and structure of a matrix material.

A surface component can comprise any material including, but not limited to metals, metal oxides, conductive polymers, electroactive materials and semiconductors. Metals and metal oxides suitable for use in the present invention include, but are not limited to titanium, titanium dioxide, tin, tin oxide, silicon, silicon dioxide, iron, iron$^{III}$ oxide, silver, gold, copper, platinum, palladium, nickel, aluminum, steel, indium, indium tin oxide, fluoride-doped tin oxide, ruthenium oxide, germanium cadmium selenide, cadmium sulfide and titanium alloy. In one embodiment, a metal is gold, and in another embodiment a metal is platinum. In one embodiment, a metal oxide is indium tin oxide (ITO). Gold, platinum, and ITO are characterized by well-characterized reactivity and electrochemical profiles.

Another consideration when selecting a material for a surface component is the chemical reactivity profile of the material. The chemical reactivity profile of a material is a consideration, because other entities, such as thiolate-containing moieties, can ultimately be associated with the surface. Additionally, it can be desirable to associate a secondary component with a surface when a heterogeneous SAM is desired. Therefore, the reactivity of a surface component toward a desired secondary component can also be a consideration. Summarily, considerations when selecting and/or designing a surface component include, but are not limited to size, material, chemical reactivity of the material, the ease with which a desired chemical moiety can associate with the surface component, and the ease with which a secondary component can associate with the surface component.

If a surface is to be a site for gradient formation, it is advantageous for the surface to be free of defects. Additionally, due to the small scales at which the various aspects of the present invention can be employed, a surface can comprise virtually any kind of structure. For example, although a surface for SAM formation comprises in one embodiment the face of a microchip or a similar flat surface, the surface of a spherical or shaped particle or a particle of any geometric shape can also serve as a surface for SAM formation. In one embodiment, when a microchip or other structure is employed as a surface, the areas of the surface upon which a SAM will be formed are coated with a material with which a matrix material can be associated (e.g., a layer of gold, ITO or other material). This might not be a consideration, depending on the chemical composition of the exposed areas of the surface. A surface component need not be entirely flat, and need only comprise a substrate suitable for forming a monolayer thereon. Thus, structures such as gold balls, which can be formed by melting the end of a gold wire, can also serve as a surface component on which a monolayer can be formed.

The matrix of a SAM can comprise any chemical compound or species. In one embodiment, a matrix material comprises a binding group, such as a thiolate moiety, which facilitates association of the matrix material with the surface. Thus, in another embodiment a matrix material comprises dodecanethiolate, although any chemical moiety comprising a thiolate moiety can also be employed (e.g., any alkanethiol). In one embodiment, matrix materials comprising a thiolate moiety are employed due to the ability of the thiolate to chemically associate with a surface such as gold. Any attachment moiety can be employed, and the selection of a suitable binding group can depend, in part, on the nature of the surface with which a matrix material will ultimately be associated. More specifically, in one embodiment a matrix material comprises a binding group that is adapted to associate the matrix material with a selected surface.

In one embodiment, a component of a matrix material that does not associate directly with the surface comprises a head group, which can comprise any chemical moiety. In one embodiment, the head group is located distal to the binding group of a matrix material. In one embodiment, then, a binding group associates with the surface and is connected to a head group via another chemical moiety. The chemical properties of the head group will dictate, in part, the nature of the SAM. Since the head group will be exposed when the binding group is associated with the surface, the head group is primarily responsible for the behavior of the SAM relative to a particle and/or a molecule disposed thereon.

The selection of a matrix material (i.e., the selection of a binding group and/or a head group) can be based on a variety of considerations, including the nature of subsequent modifications to the SAM, such as the formation of a gradient. Additionally, if a SAM will comprise a part of a gradient, the chemical properties (electrostatic, hydrophobic/hydrophilic, etc.) of the gradient can also play a role in selecting a matrix material.

A matrix material need not comprise a straight chain moiety and can comprise any desired structure and functional group(s). Some additional examples of suitable matrix materials include organomercaptans such as diacetylenic thiols, e.g., ω-functionalized n-alkanethiols. Such compounds can comprise an unlimited number of backbone carbon atoms. Representative compounds comprise a group that is hydrophilic such as $HS(CH_2)_nCOOH$ or $HS(CH_2)_nCH_2OH$ where n is any integer from 1 to 50, in one embodiment n is 1, 2, 3, 4, 5, 6, 7, 8, 9, 10, 11, 12, 13, 14, 15, 16, 17, 18, 19 or 20; a group that is hydrophobic such as $HS(CH_2)_nH$ where n is any integer from 1 to 50, any integer from 1 to 50, in one embodiment n is 1, 2, 3, 4, 5, 6, 7, 8, 9, 10, 11, 12, 13, 14, 15, 16, 17, 18, 19 or 20; a group that is electroactive such as ferrocenyl; a group that specifically binds to other moieties such as an antibody fragment, single-stranded DNA, biotin, nickel nitrilotri-acetic acid; a group that resists non-specific adsorption such as oligoethylene glycol; or a group that is chemically reactive such as amino, pentafluorophenyl ester, N-hydroxysuccinimide ester or carboxylate. Thus, different surface-matrix material complexes can be formed. For example, as discussed herein, thiols can be disposed on metals such as gold, silver, copper, platinum, palladium and nickel. In other embodiments of a SAM, thiols can be disposed on indium tin oxide, isocyanides can be disposed on platinum, carboxylic acids can be disposed on metal oxides, hydroxamic acids can be disposed on metal oxides, trichlorosilanes can be disposed on silica and trialkoxysilanes can be disposed on silica, to name just a few embodiments. It is noted that the above list is presented for illustrative purposes and is not an exclusive list of all materials that can be employed to form a SAM of the present invention.

Sometimes, it will be desirable to form a homogeneous SAM. A homogeneous SAM comprises a surface bearing a single species of matrix material. In one embodiment, a homogeneous SAM comprises a matrix material of one uniform chemical species. Other times, it will be desirable to form a heterogeneous SAM. In this embodiment, a heterogeneous SAM comprises a matrix material comprising two or more chemical species. In either case, however, the matrix material can comprise an attachment moiety.

Preparation of a SAM can be readily achieved, due to the chemical composition of the SAM. More specifically, a SAM is a self-assembled structure. Thus, under suitable conditions, a SAM spontaneously assembles on a surface. Upon formation of a SAM, a surface can be wholly or partially covered with a matrix material. Additionally, in one embodiment a SAM forms areas of uniform coverage by a matrix material. Uniformly covered areas are identified as areas in which matrix material coverage is consistent and free from defects, such as pitting, rifts, and general unevenness in coverage by the matrix material.

IV.B. Patterned Desorption and Replacement Lithography

Figure 1B:
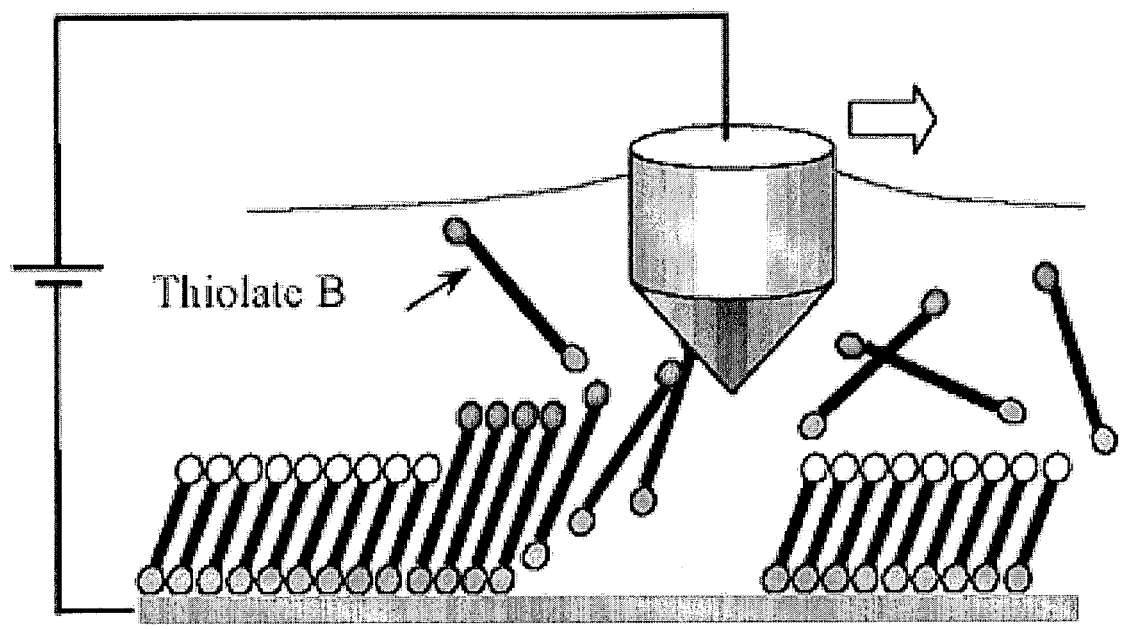
FIG. 1B is a schematic diagram depicting the replacement of matrix material with a patterning material.
Figure 1C:
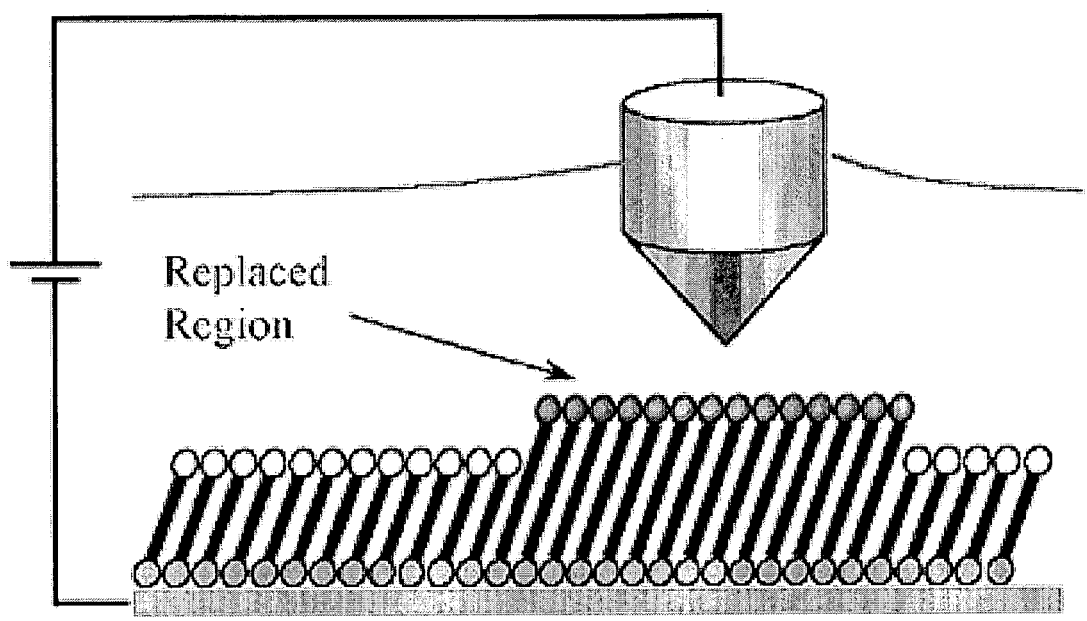
FIG. 1C is a schematic diagram depicting a pattern comprising matrix material and patterning material.
Figure 1D:
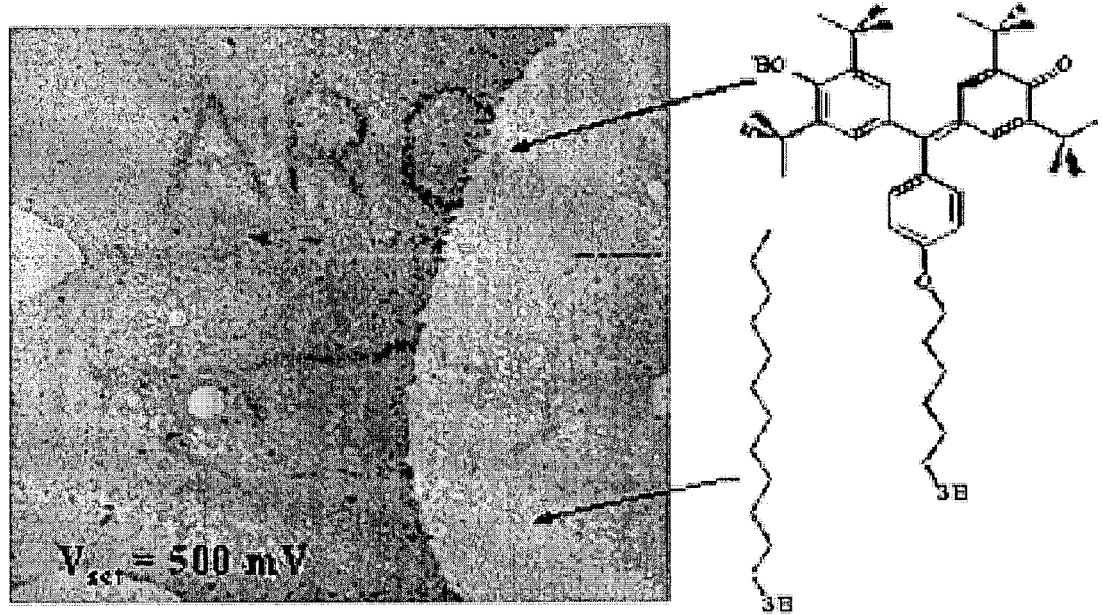
FIG. 1D is a micrograph depicting a pattern formed by an electroactive galvinol-terminated thiol in a SAM comprising dodecanethiolate disposed on a gold surface.
Figure 2:
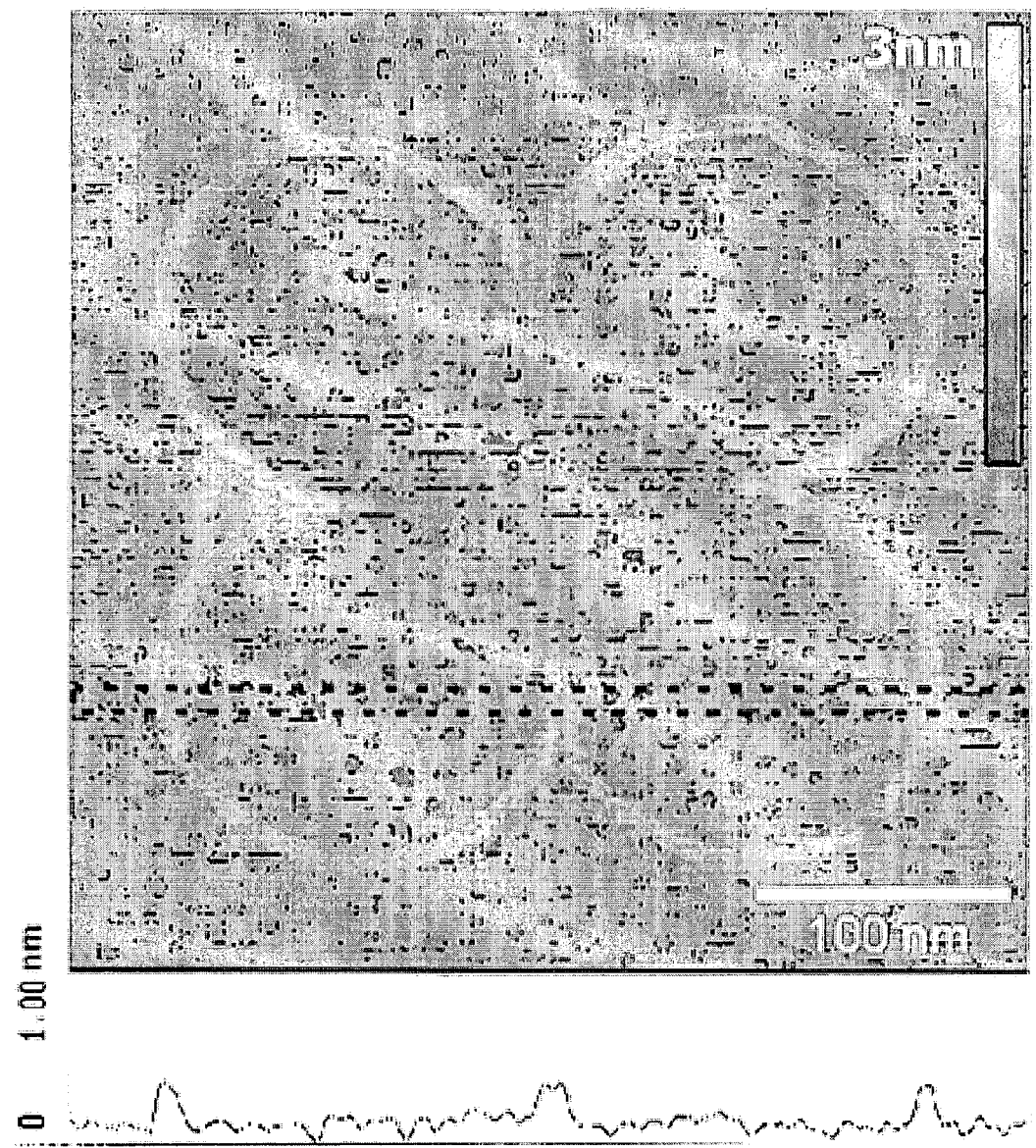
FIG. 2 is a 400 nm×400 nm scanning tunneling microscopy (STM) image of a quarterfoil test pattern of ferrocenyl-undecanethiol ($FcC_{11}SAc$) replaced into $C_{12}S$-SAM. Immediately below is an apparent height profile for the average of the horizontal line scans between the dotted lines on the image.

Patterned desorption and replacement lithography techniques are employed in accordance with the present invention to prepare a pattern or gradient on a surface bearing a SAM comprising matrix material. A representative replacement lithography methodology that can be employed to prepare these gradient structures is illustrated in FIGS. 1A–1C. A molecular replacement technique comprises in one embodiment providing a SAM disposed on a surface, employing an STM tip to desorb SAM matrix material in a desired pattern, and substituting a patterning material for the material that was desorbed. The structure formed will then comprise a monolayer from which an amount of matrix material has been removed in a desired pattern; patterning material can fill in the regions from which matrix material has been desorbed.

An advantage of this method is that the substitution can be performed concurrent with desorption of matrix material and in real time. Alternatively, if a gradient or other structure is to be prepared, the desorption of SAM matrix material, a process that can be employed to form a pattern on the surface, can be followed by, or concurrent with, substitution of matrix material with a patterning material adapted to provide a driving force that varies with position within the pattern, again in real time. These and other applications are discussed further herein below.

IV.B.1. Patterned Desorption

In one aspect of the present invention, patterned desorption broadly involves desorbing matrix material from a SAM in a desired pattern. The displacement is achieved in one embodiment by employing a STM tip. In one aspect of the present invention, a pattern can be formed by performing the following steps. Initially, a surface bearing a monolayer of matrix material is provided. Suitable surfaces and matrix materials are described throughout the present disclosure, but in one embodiment a surface comprises an electrochemically active material when patterned desorption is employed. After performing any desired preparation of the surface, an STM tip is brought into the proximity of the SAM. The tip-substrate bias is then raised to a voltage level suitable for desorption of matrix material from the surface. Thus, the desorption voltage level can vary with the composition of a SAM. For example, when a SAM comprises dodecanethiolate, the tip-substrate bias can be varied from a level suitable for imaging the surface (typically about +1 V) to about +3 V. While the tip-substrate bias is at this level, the tip can be rastered in a desired pattern to produce a patterned desorption of matrix material. The resultant pattern can form a component of a gradient or other structure. Patterned desorption can be accompanied by concurrent substitution of the matrix material with a patterning material, as described below.

IV.B.2. Replacement Lithography

Generally, replacement lithography comprises replacing or substituting matrix material of a SAM or other heterogeneous or homogeneous layer for another material. By way of a specific example, replacement lithography can be employed to replace regions of dodecanethiolate (a matrix material), desorbed in a desired pattern, with ferrocenyl-undecanethioacetate (a patterning material).

As disclosed herein below, there are a variety of methods of substituting a patterning material into the SAM. In one embodiment, replacement lithography (ie. desorption of matrix material and substitution of patterning material therefor) can be performed under a non-polar, low dielectric fluid, such as dodecane. This fluid can also serve as a solvent for a patterning material of interest and can additionally facilitate imaging with negligible leak current (<1 pA) into the solvent. The selection of a suitable solvent can depend, in part, on the chemical properties of the matrix material. It is noted that any solvent can be employed in a substitution operation due, in part, to the low concentration of the patterning material in that solvent. For example, thiols containing polar head groups (e.g. carboxylate) can be dissolved in solvents that are completely non-polar (e.g. dodecane and other oils) at concentrations acceptable for replacement lithography.

In one embodiment of a replacement lithography method, prior to substitution of patterning material for matrix material, a surface bearing a monolayer can be imaged in order to locate an area free of substrate terraces or defects that is suitable in size and composition for a desired pattern (as depicted in FIG. 1A). A surface can then be exposed to a solvent comprising a patterning material. Selection of a suitable solvent can depend, in part, on the nature of the monolayer, the nature of the matrix material and the nature of the patterning material; although, as noted above, the concentration of species dissolved in the solvent facilitates the use of any desired solvent. In one embodiment, when a monolayer is non-polar, a solvent can comprise a non-polar, low dielectric fluid.

An STM tip can then be situated in contact with the solvent and above the monolayer. As the tip is rastered in a desired pattern, thiolate desorption from a surface can be induced by subsequently elevating the tip-substrate bias to about +3 V (FIG. 1B). This localized desorption, in conjunction with the chemical nature the solvent and the patterning material, allows the patterning material molecules in solution (which comprise in one embodiment a thiolate moiety or other moiety adapted to facilitate association of the patterning material with the surface) to spontaneously adsorb into the freshly exposed surface regions (i.e., a pattern of desorbed matrix material), thereby creating a monolayer having a different composition. Once a desired lithographic pattern is formed, the STM parameters can be returned to the lower bias parameters and the resultant structure can be imaged (FIG. 1C). Imaging the resultant structure can facilitate an assessment of the effectiveness of the incorporation of the patterning material.

Figure 4:
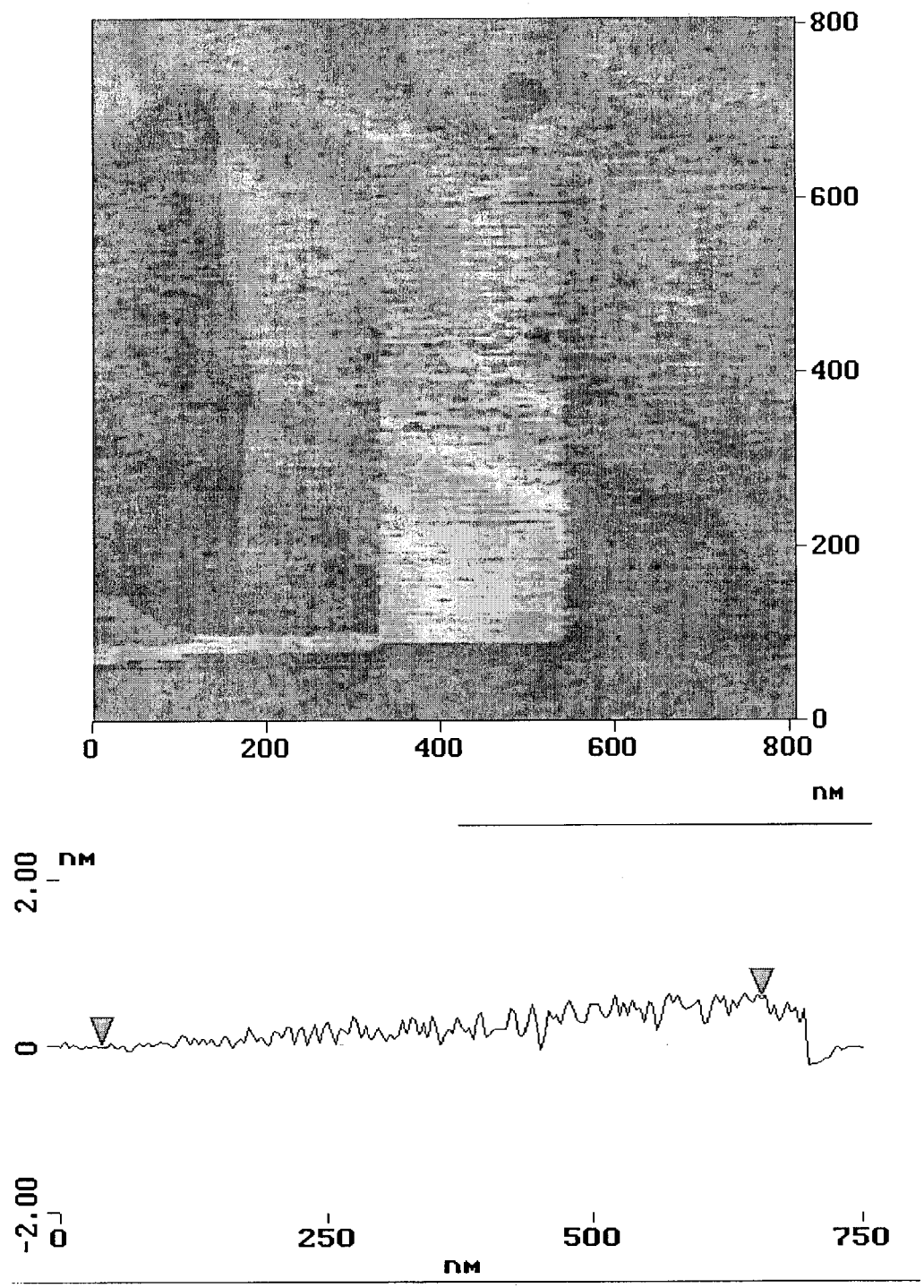
FIG. 4 is a micrograph depicting a gradient formed by employing the replacement lithography methods of the present invention.

By way of specific example, in the gradient of FIG. 4 was prepared by replacement lithography. In this example, dodecane solutions of thiol (about 1 mM in thiol) were chosen as the solvent/patterning material, since dodecane is nonpolar and is a very low dielectric medium, thus avoiding leak current with the solution. SAMs comprising decanethiolate ($C_{10}$S-SAM) and dodecanethiolate ($C_{12}$S-SAM) were grown on an atomically flat facet on an annealed gold ball. These SAMs were imaged repeatedly under dodecane solutions without apparent change in their appearance under conditions of setpoint bias of +1 V (positive substrate bias) and setpoint current of about 6–8 pA. Upon changing the bias to +3.0 V or slightly higher (up to +4.0 V), substitution of the thiolate on the surface for the different thiol in solution occurred. This substitution was observed by scanning the tip in one area at the higher voltage, reducing the setpoint voltage back to 1 V and scanning the tip across a larger area. By rastering the tip in a defined pattern, features with about 10–15 nm resolution can be generated. This procedure of desorbing matrix material can be employed to generate a variety of patterns. The efficiency of replacement can depend on at least three parameters: (1) replacement bias, (2) lithographic scan rate, and (3) relative humidity present in the atmospheric chamber surrounding the STM head. Each of these parameters is discussed further herein below.

Another advantage of the present invention is that the substitution techniques disclosed herein can be performed in real time. That is, the desorption process and the substitution processes can be performed at the same time. Thus, patterning material can "fill in" a desorbed pattern, effectively as it is formed. Other STM-based techniques do not afford this ability.

IV.C. Representative Patterning Materials

Virtually any material can be employed as a patterning material in the present invention. In one embodiment, a patterning material comprises a head group and a binding group. Like the binding group of a matrix material, a binding group of a patterning material facilitates association of the patterning material with the surface, upon desorption of matrix material. In one embodiment, a binding group comprises a thiolate moiety, which facilitates association of the matrix material with the surface. Thus, a patterning material can comprise dodecanethiolate, although any chemical moiety comprising a thiolate moiety can also be employed (e.g., any alkanethiol, alkenethiol, alkynethiol, and substitute versions thereof). Patterning materials comprising a thiolate moiety can be employed due to the ability of the thiolate to chemically associate with a surface such as gold. However, any binding group can be employed, and the selection of a suitable attachment moiety can depend, in part, on the nature of the surface with which a matrix material will ultimately be associated. In one embodiment, a matrix material comprises a binding group that is adapted to associate the patterning material with a selected surface.

A head group of a patterning material can comprise any chemical moiety. In one embodiment, the head group of a patterning material is located distal to the binding group. In another embodiment, a binding group associates with the surface and is connected to a head group via another chemical moiety. The chemical properties of the head group dictate, in part, the nature of a gradient formed. Since the head group can be exposed when the binding group is associated with the surface, the head group is primarily responsible for the behavior of the gradient relative to a particle and/or a molecule disposed thereon.

The selection of a patterning material (i.e., the selection of a binding group and/or a head group) can be based on a variety of considerations, including, but not limited to the nature of subsequent modifications to the patterning material or a gradient comprising a patterning material. Additionally, the desired chemical properties (electrostatic, hydrophobic/hydrophilic, etc.) of the gradient can also play a role in selecting a patterning material.

Suitable patterning materials can also comprise, for example, absorptive molecules (and, concurrently, emissive molecules), electroactive molecules, molecules with varying hydrophobic and hydrophilic properties, and molecules adapted to form multimeric structures, to name just a few. If the patterning material is to be employed in a dynamic gradient, the material can be responsive to a stimulus, such as a change in pH or the application of a bias. Thus, the choice of a patterning material can depend on the role the patterning material will ultimately play. For example, if a patterning material will ultimately form a component of a gradient, which will in turn form a component of a molecular machine, a desired property of a patterning material can be the ability to alter the reactivity of the material towards another material. These and other examples are described in the following sections.

IV.C.1. Absorptive Molecules

A patterning material can comprise an absorptive molecule. Absorptive molecules can comprise fluorescent and phosphorescent molecules, as well as those that absorb and/or emit energy at a given frequency. For example, it might be desirable to generate a pattern of molecules on a surface that absorb and/or emit energy at a given wavelength. In this case, the matrix material that is replaced can be nonabsorptive. After desorbing matrix material and replacing the desorbed material with a patterning material, as described herein above, the surface comprises a patterning material that absorbs and/or emits energy at a given wavelength and conforms to the pattern formed by the desorption of matrix material.

A species of absorptive molecule can also serve as a patterning material, even when a matrix material is itself an absorptive species. In this case, a patterning material can comprise an absorptive species that absorbs and/or emits energy at a wavelength different from that of the matrix material. More than one species of absorptive patterning material can exist on a single surface. Thus, on a single surface, absorption and/or emission at two or more wavelengths can be achieved.

Representative patterning materials comprising absorptive species include, but are not limited to conventional dyes of any type currently used as molecular probes, such as thiol-capped coumarins, porphyrins, cyanines, etc., and/or fluorescent nanoparticles such as cadmium sulfide and cadmium selenide.

IV.C.2. Multimeric and Multilayered Structures

Most of the patterning materials discussed thus far comprise monomeric species. However, a patterning material can also comprise a species that is adapted to form multimeric species. When such a species is employed as a patterning material, a resulting surface can comprise multimeric species in regions in which patterning material has been substituted for matrix material. Alternatively, a matrix material can be selected that is adapted to form multimeric structures.

When a multimeric structure is desired in a region of patterned desorption or a region of matrix material, there are at least two strategies for placing the species in a desired area of a surface. First, the multimeric species can be formed (i.e., multimerized) before it is exposed to the monolayer (which can comprise matrix material or patterning material) present on a surface. The multimerization can be achieved by derivatizing a compound and linking two or more compounds together. Subsequently, the multimeric species can be disposed in a solvent and associated with the surface in the regions from which matrix material is desorbed or in regions of the matrix material.

In a second strategy, a multimeric species can be "grown" in situ following replacement of matrix material with a replacement compound adapted to form multimeric species or after formation of a SAM comprising matrix material. Such multimers can initially be formed end-to-end (ie. head group-to-head group or head group-to-binding group). A patterning material or a matrix material that is adapted to form multimeric species can also comprise compounds adapted to form branched structures.

In one application of this second strategy, a patterning material is disposed in a solvent. The patterning material is associated with a surface as described herein above. A property of the patterning material is that it comprises a reactive functional group at a point on the material that is distal to the surface. Once the patterning material forms a component of a monolayer on the surface, the material can form a scaffold for the preparation of a multilayered structure extending beyond the one molecule thick dimensions of the matrix material on the surface.

Once a patterning material comprising a reactive functional group has been associated with the surface, a second material can be reacted with the reactive functional group of the patterning material to form multimeric and/or multilayer structures. The second material can optionally comprise the same chemical composition as the patterning material. The conditions for such a reaction are dictated, in part, by the nature of the reactive group. In one embodiment, a reactive functional group is selected such that a secondary material (which can also be the same chemical species as the patterning material) can be reacted with, and covalently joined to, the patterning material without interacting with the matrix material. A secondary material can comprise virtually any chemical species, although it should be compatible with a chosen reactive functional group. In one embodiment, a secondary material comprises a form of the matrix material derivatized with a reactive functional group.

When a secondary material is reacted with a patterning material, the secondary material is covalently joined with the patterning material. Physically, this joining extends the dimensions of the patterning material and, depending on the nature of the secondary material, can extend the dimensions by angstroms or nanometers. Structurally, this extension typically takes the form a structure extending away from the one molecule thick monolayer of matrix material. Effectively, the joining of a secondary material with a patterning material leads to a "raised" structure on a surface, with matrix material extending to a first degree away from the surface (in a homogeneous monolayer, the first degree comprises the length of one matrix material molecule) and secondary material extending the length to a second degree. This imparts a "raised" effect to the surface. Multiple rounds of extension can be performed (if the secondary material comprises a reactive functional group) in order to extend the dimensions of secondary material to any desired distance from the surface or from the matrix material.

In an alternative embodiment, a monolayer can comprise a matrix material comprising a reactive functional group distal to the surface and an unreactive patterning material. When this arrangement is employed, a patterned structure can be created, with the patterning material forming the bottom of the desorbed pattern and multiple layers of matrix material forming the sides of the pattern. Since formation of multimeric or multilayer structures extending from the patterning material is not possible in this arrangement, extension of the matrix material away from the surface can be achieved by forming multilayer and multimeric structures extending from a scaffold of matrix material. This structure can comprise patterning material at a first distance from the surface (typically, the length of a molecule of patterning material) and multiple layers of matrix material at a second distance from the surface, extending the matrix material beyond the first distance.

A multilayered structure can comprise alternating layers of different patterning materials. Patterning materials can be different in their chemical profiles (e.g., redox properties), which can be a property of a functional group element of a patterning material. In a multilayered structure incorporating patterning material, the patterning material comprises in one embodiment a functional group (e.g., a ferrocenyl or galvinoyl group) and a group adapted to associate the patterning material with either a surface or a functional group of a patterning material.

V. Crafting a Gradient Structure

A gradient structure can be formed on a surface by employing the methods of the present invention. As discussed further herein below, a gradient structure can play a role in a variety of applications, such as synthetic organic chemistry on a molecular scale and "lab on a chip"-type applications, to name just a few. A gradient can be formed on a surface comprising a monolayer or a surface without a monolayer. When a monolayer comprising a matrix material is present on a surface, a region of patterned desorption can be formed in the matrix material. A gradient comprising a patterning material comprising one or more functional groups different from those of the monolayer can then be formed concurrently formed therein. When a monolayer is absent from a surface, a gradient can be formed directly on the surface itself.

A method of making a gradient on a surface is thus disclosed in accordance with the present invention. In one embodiment, the method comprises disposing a self-assembled monolayer (SAM) on a surface; and distributing a patterning material in the SAM, the patterning material defining a gradient on the surface. Additional embodiments for forming gradients are described herein below.

V.A. Preparation of a Surface and a Monolayer Comprising a Matrix Material

A gold surface is an exemplary surface for the methods and gradients of the present invention. However, other surfaces can be employed in the present invention. For example, indium tin oxide (ITO) can be employed as a surface. ITO is a transparent conductor and can impart an advantage in characterization of the surface, since both electrochemical and transmission optical methods are available. Overall, detection of gold, semiconductor molecules, and/or nanoparticles can be accomplished conveniently on ITO by electrochemistry, scanning tunneling microscopy, scanning electron microscopy, and Auger microscopy. Also, bonding to metal oxides is very stable, which offers additional advantages.

After selecting a suitable surface material, the surface can be prepared for monolayer formation. In one embodiment, facets of the surface are annealed and the surface is free of defects in order to ensure optimal monolayer formation. This annealing can be achieved by exposing the facets to a $H_2$ flame prior to monolayer deposition. By way of specific example, an end of a gold wire (0.5 mm, 99.9985%, Alfa Aesar, Ward Hill, Mass., United States of America) can be melted in a $H_2$ flame to create a small faceted ball. The ball can be subsequently zone refined to yield $Au^{3+}$ facets along the equatorial region of the ball.

Following preparation of the surface, a matrix material can be associated with the surface under conditions that will facilitate formation of a monolayer. In one embodiment, a matrix material is adapted to form a self-assembled monolayer. That is, a matrix material is adapted to form a monolayer associated with the surface spontaneously and without the need to perform involved chemical reactions.

In one embodiment of the present invention, a surface comprises a gold ball, a matrix material comprises a thiolate binding group, and a representative procedure for the formation of a monolayer comprises the following. A freshly annealed ball is placed in a 1 mM $C_xH_ySH$ ethanolic solution, where X and Y are integers (e.g., $C_{12}H_{25}SH$, Aldrich, St. Louis, Mo., United States of America), refluxed for 1 hr (Weiss et al., (1996) Ann. NY Acad. Sci. 852:145), and allowed to cool to room temperature. The faceted ball is then removed, rinsed with copious amounts of absolute ethanol (AAPER Alcohol and Chemical Co., Shelbyville, Ky., United States of America), and dried in a stream of $N_2$. Following this or another procedure, a surface comprising a monolayer can be prepared. This structure can then form a substrate for patterned desorption and/or gradient formation, as described herein below.

Although the gradients and methods of the present invention can employ organothiolates on a gold surface, metal oxide surfaces can also be employed. Association with metal oxides is very stable, and offers an advantage in the repetitive operation of the gradients and gradient-based machines of the present invention. In one embodiment, a procedure for preparing a metal oxide surface is similar to single layer coverage on metal oxide surfaces employing zirconium tert-butyl butoxide coatings, which can be prepared as an aerosol under reduced pressure of $10^2$ Torr. Additionally, metal tert-butoxides do not form multilayers, which might be desirable in certain applications.

Following coverage with a monolayer, the surface layer can be further covalently modified using alkyl phosphonates, carboxylates, or other compounds. This procedure provides for covalent surface attachment of mixed monolayers on a variety of metal oxide surfaces (Tao, (1996) Phys. Rev. Lett. 76: 4066). Moreover, routine exploration of several surface functionalization strategies can solve problems that might be encountered during certain investigations, such as phase separation.

V.B. Patterned Desorption

After a suitable monolayer is prepared on a surface, the regions of matrix material can be desorbed so as to form a pattern in the monolayer by employing STM methods and equipment. In one embodiment, imaging and pattern formation can be performed at room temperature by employing an STM (e.g., a NANOSCOPE IIIa™, available from Digital Instruments, Santa Barbara, Calif., United States of America) in dodecane with mechanically cut Pt/Ir tips (90:10, 0.25 mm, Alfa Aesar, Ward Hill, Mass., United States of America). The tip can be rastered over the surface in a desired pattern to create a desorption pattern of desired dimensions and location. During the rastering, the tip-substrate bias can be elevated from levels suitable for imaging a surface (e.g., about +1 V) to a level suitable for desorbing matrix material from the surface (e.g., about +3 V for a dodecanethiolate matrix material).

The amount of matrix material that is desorbed from the surface can be dependent on the rastering pattern. For example, if it is desired to make a pattern that has equal dimensions, the tip can be rastered in the x direction motion, while gradually altering the tip's position in the y direction to reach a dimension equal to that of the x dimension. Any pattern is possible via the methods of the present invention and any geometry can be generated. A pattern can form for a component of a gradient, as disclosed in the subsequent sections.

In one embodiment, substitution of matrix material with another chemical compound (i.e., a patterning material) is performed concurrent with desorption of matrix material. In this case, the patterning material can be disposed in a solvent that contacts the matrix material and the STM tip. In one embodiment, conditions for performing a substitution operation comprise maintaining relative humidity between 50 to 60% (which can be monitored with a hygrometer). Nitrogen gas can be bubbled through a gas dispersion tube into a closed vessel containing MILLIQ™ water (18 $\mu cm^2$), and can feed the moist outlet gas into the atmospheric chamber containing the STM. Micromolar concentrations of solutions comprising a patterning material in a solvent can be employed.

V.C. Forming a Gradient

In one embodiment of the present invention, a gradient can be formed by disposing a partial self-assembled monolayer on a surface followed by completion of the self-assembled monolayer with a second, different component to make a new, heterogeneous SAM that comprises a chemical gradient structure gradient. In another embodiment of the present invention, a gradient can be formed by disposing a self-assembled monolayer on a surface followed by partial removal of the SAM and replacement with a second, different component to make a new, heterogeneous SAM that comprises a chemical gradient structure. Further details of these two embodiments, as well as general methods of forming a gradient are presented hereinbelow.

After forming a pattern in a SAM by desorption of matrix material, or alternatively concurrent with patterned desorption, a gradient can be formed in the region of the surface comprising the pattern. The precise composition of a gradient can vary and it is not required that a gradient comprise any one single patterning material. As noted, a gradient can be formed in a desorbed pattern concurrent with the formation of the desorbed pattern itself. Further, a gradient can be formed in a pattern by varying the scanning rate and/or the tip-substrate bias of the STM tip. In this aspect of the present invention, a patterning material can be disposed in a solvent and associated with a monolayer-covered surface as matrix material is desorbed therefrom. Alternatively, a gradient can be formed on a surface independent of the presence of a pattern. That is, a gradient can be formed directly on a surface, without confining the gradient to a structure defined by a pattern. In another aspect of the present invention, a gradient can even be formed directly on a monolayer itself.

Each of the following techniques can be applied for applications at a given scale; however, this is not a requirement. More specifically, some of the disclosed substitution techniques operate best on one scale, while other techniques work better on another scale. For example, replacement lithography is can be employed for a nanometer-scale replacement operation on an electroactive surface. Microcontact printing, vapor diffusion, shuttered evaporation and other techniques work more efficiently on the 100 nm to micron-scale. Although each of these techniques has a preferable scale, any of the techniques can be employed in gradient formation on any scale. Thus, although all of the disclosed strategies for making gradients can be employed on any scale, each is ideally applied on one length scale.

V.C.1. Vapor Deposition Method of Gradient Formation

Figure 5A:
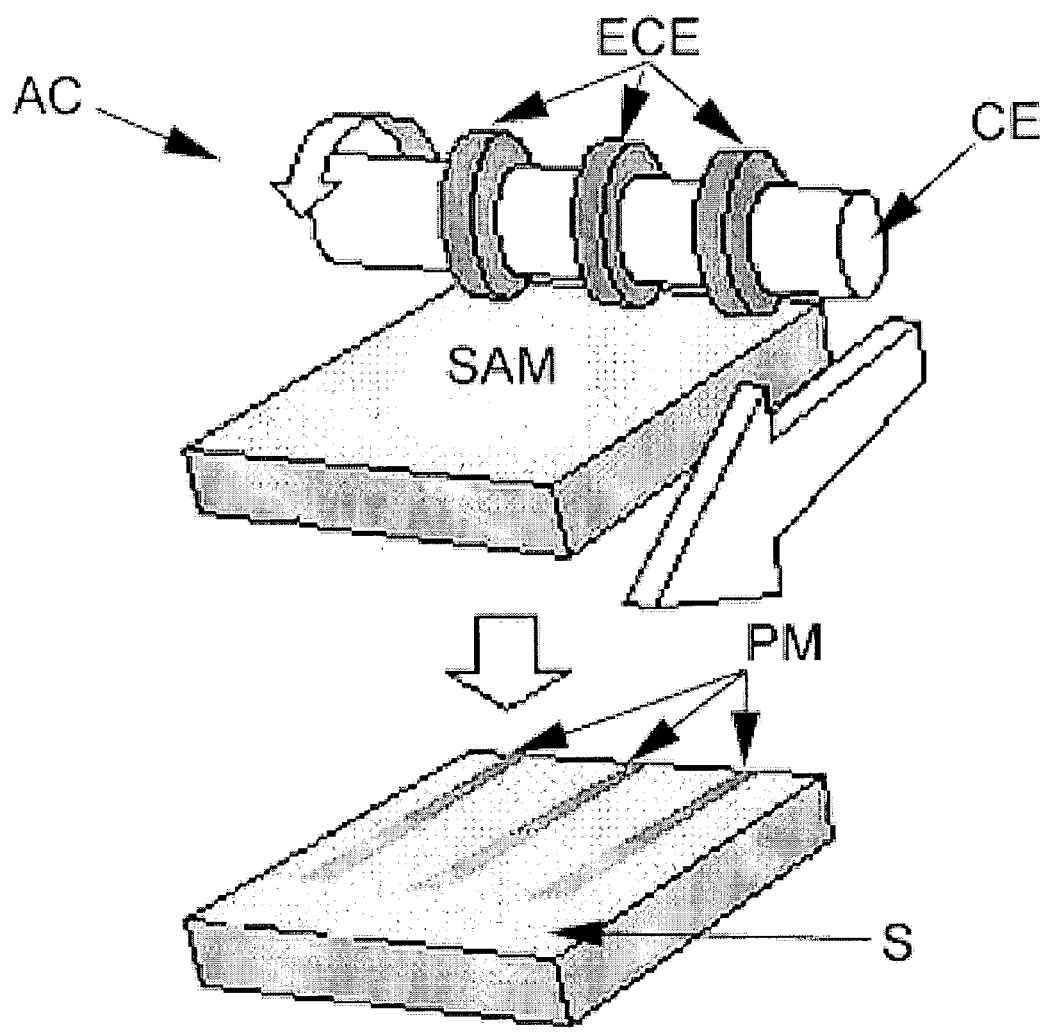
FIG. 5A is a schematic diagram depicting the process of gradient formation via a microcontact printing method of the present invention.
Figure 5B:
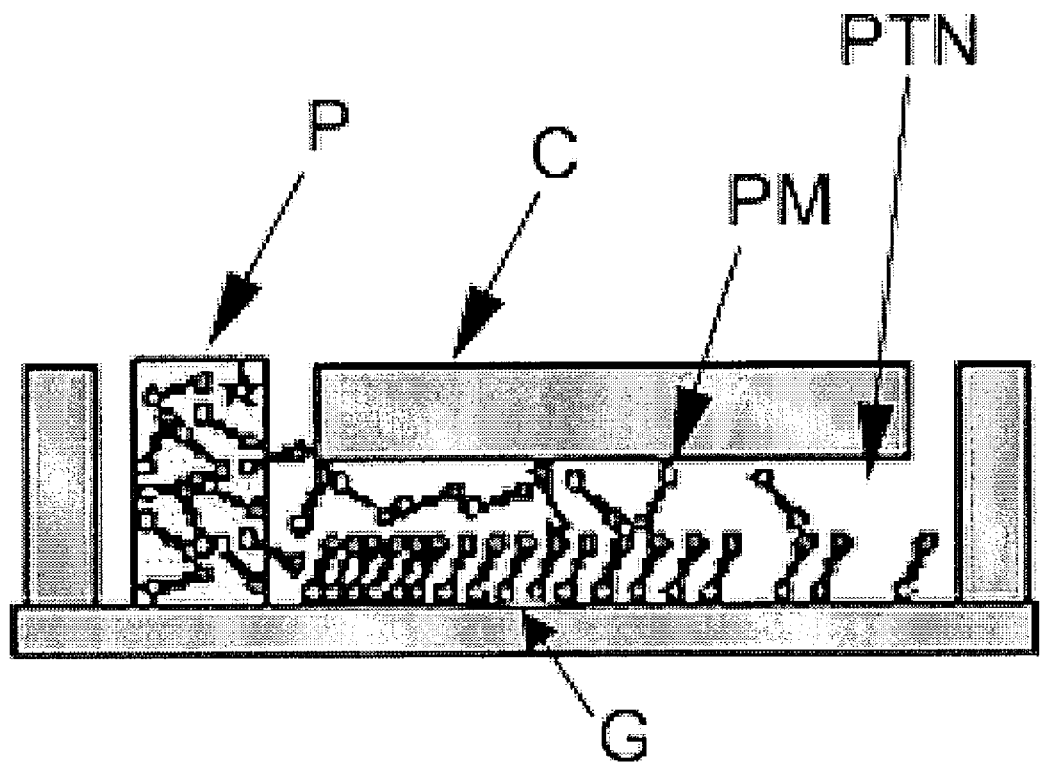
FIG. 5B is a schematic diagram depicting the cross section of a channel in which a vapor diffusion method of the present invention is being employed to form a gradient. The block marked with a star is a plug of low-density PDMS impregnated with a low to medium vapor pressure thiol molecule.

Gradients on the 500 nm to 1 mm length scale can be formed by employing a vapor diffusion technique, depicted schematically in FIG. 5B. A major difference between the present method and the prior art methods of gradient formation is that in the present method, a vapor comprising a patterning material (e.g., a volatile thiol) is ushered down a patterned channel, as depicted in FIG. 5B. By controlling and accounting for (1) the relative exposure time, (2) patterning material vapor pressure, and (3) the use of any pressure to encourage mobility of a patterning material along the length of a pattern, a gradient can be created.

Broadly, formation of a gradient on a surface can be achieved by employing vapor diffusion techniques. In one embodiment of the present invention, a pattern is prepared by desorbing matrix material from a surface. A plug of material permeated with a patterning material is placed in the proximity of the pattern. Conditions in the area of the pattern are then set to levels such that the patterning material can diffuse out of the plug and associate with a surface that was exposed during formation of the pattern. The formed gradient comprises a greater concentration of patterning material in the areas closer to the plug, while the gradient comprises a lower concentration of patterning material in the areas more distal to the plug.

It is not necessary that a pattern be formed on a surface in order to employ the vapor diffusion methods of gradient formation. A gradient can be formed by these methods directly on a surface. In this embodiment, no preparation of a surface need be performed beyond inspection of the surface to find a defect-free region for gradient formation and annealing of facets, as required.

Referring now to FIG. 5B, in accordance with the present invention, a method of making a gradient on a surface by vapor diffusion is provided. In one embodiment, the surface comprises a pattern formed in a self-assembled monolayer SAM disposed on the surface, the surface being maintained at a set of one or more conditions. The surface can comprise any material. In one embodiment, the surface comprises gold, and in another embodiment, the surface comprises ITO. Similarly, a SAM can comprise any matrix material, with the caveat that a SAM matrix material comprises a binding group that facilitates association of the matrix material with the surface (e.g., a thiolate group). Suitable matrix materials include, but are not limited to dodecanethiolate. In one embodiment, a matrix material comprises a thiolate binding group for association with a surface. Formation of a pattern can be achieved by employing the STM-related methods disclosed herein above.

Continuing with FIG. 5B, a plug P comprising a volatile patterning material PM is positioned in pattern PTN. In one embodiment, a patterning material PM comprises a thiolate binding group, although patterning material PM can comprise any material adapted to associate with the surface. Thus, as a general rule, patterning material PM comprises a material that is compatible with the chemical properties of a surface to provide association of the material with the surface. In one embodiment, patterning material PM is disposed in plug P of material, which is placed in pattern PTN. Plug P can comprise, for example, low density poly (dimethylsiloxane) (PDMS) or a similar material. Plug P can be impregnated with a low to medium vapor pressure patterning material PM. For example, patterning material PM comprises in one embodiment a thiol or other binding group adapted to associate the material with the surface and a desired head group.

Continuing with FIG. 5B, the pressure can be varied to thereby deposit variable concentrations of patterning material PM at different points on pattern PTN. When patterning material PM comprising a volatile material is employed, the relative exposure time and thiolate vapor pressure can be controlled. Pressure can also be employed to encourage mobility along the pattern to thereby form a gradient. In this method, an optional cover element C can be employed. Cover element C can comprise a workpiece adapted to inhibit diffusion of patterning material PM out of the pattern, while permitting diffusion out of plug P. In one embodiment, cover element C comprises a material that will not take up patterning material PM, and will instead operate to generally contain diffusing patterning material PM to a pattern PTN. FIG. 5B depicts an exemplary cover element configuration when the cover element C is in place for gradient formation.

In the present method, the local environment of the pattern, in which a plug comprising a volatile patterning material is disposed, can be maintained at a given pressure. In one embodiment, the pressure is such that patterning material does not diffuse out of the plug, which is placed at a first end of the pattern, until it is desired that the material leave the plug. After placement of an optional cover element, the pressure can be varied to facilitate diffusion of patterning material out of the plug and down the pattern towards a second end. The variation in the pressure at which a system is maintained can be dependent on the vapor pressure of the patterning material. Thus, by varying the pressure, the rate and amount of material diffusing out of the plug can be controlled.

In operation, the pressure can be varied such that a larger concentration of patterning material can be disposed in the area nearest the plug, while a lesser concentration of patterning material can be disposed in a area distal to the plug. Since the patterning material can comprise a functional group adapted to associate the material with the surface, the material can form regions of high and low patterning material concentration. Following association of the material with the surface via the binding group, the cover element can be removed, if a cover element was employed.

When a gradient is formed directly on a surface itself and is not formed in the space of a pattern formed in a monolayer, the surface can be covered with a matrix material, following formation of the gradient. The matrix material can be selected and applied such that the matrix material will not associate with the gradient, but will associate with the surface. In this way, the areas of the surface that do not comprise a gradient can be covered with matrix material and can surround the gradient.

V.C.2. Microcontact Printing Method of Making a Gradient

In microcontact stamp lithography, stamps are fabricated by casting a replica in poly(dimethylsiloxane) (PDMS) of a master with a negative of the desired pattern. In the one prior art example of microcontact stamping used for lithography, the PDMS stamp is inked with an alkanethiol (hexadecanethiol) and that material is transferred to a gold substrate by transient contact between the stamp and the gold substrate (Kumar & Whitesides, (1993) *Appl. Phys. Lett.* 63: 2002–2004).

The present method can be extended to partial deposition of a SAM or a gradient via a microcontact-printed stamp and dilute patterning material solution, as depicted in FIG. 5A. Broadly, a stamp can be inked with a very dilute solution of one of the components and rolled across the surface, increasing or decreasing the velocity during the process. By rolling the stamp progressively more rapidly over the surface and a knowledge of the relative effect of contact time on SAM formation, gradients of different "slopes" (e.g., how quickly the surface composition changes from 100% of a first component to 100% of a second component) can be prepared.

In accordance with the present invention, a process for making a gradient on a surface by microcontact printing is provided. Initially, a surface is provided. Suitable surfaces include, but are not limited to gold, ITO, metal oxides, and combinations thereof. However, any material can be employed. In one embodiment, the surface is free from defects such as pitting and, unless desired, oxide coatings and other contaminants are removed from the face of the surface. As with all methods of the present invention, any defects in the surface can be removed prior to performing the steps of the method, for example by annealing the facets of the surface.

An application component can then be provided. An application component is the element that will transfer a gradient material to the surface. An application component can comprise any material including, but not limited to PDMS. It is noted that an application component can comprise more than a single element. The application component is then contacted with a patterning material to form a coated application component. This step can be referred to as "inking" the application component. Inking the application component can be achieved by contacting the application component with patterning material.

For example, as depicted in FIG. 5A (a schematic that is not to scale), an application component AC can comprise a cylindrical element CE with one or more additional cylindrical elements ECE encircling the circumference of cylindrical element CE. In this embodiment, cylindrical elements ECE encircling the circumference of cylindrical element CE contact the surface S and apply a pattering material PM to the self-assembled monolayer SAM disposed on surface S.

Continuing With FIG. 5A, patterning material PM can be disposed on surface S itself, but in this example, is disposed on the self-assembled monolayer SAM that is disposed on surface S. After an application component AC has been inked, it can be sequentially and continuously contacted with contiguous regions of self-assembled monolayer SAM disposed on surface S until patterning material PM is transferred from application component AC to self-assembled monolayer SAM disposed on surface S. Application component AC can be dimensioned such that a desired area and/or region of the application component AC contacts the patterning material PM during an inking process.

Continuing with FIG. 5A, patterning material PM can be transferred to self-assembled monolayer SAM disposed on surface S by initiating a rolling motion of application component AC. As application component AC in contact with self-assembled monolayer SAM disposed on surface S is moved along self-assembled monolayer SAM disposed on surface S, the concentration of patterning material PM transferred to a given point on self-assembled monolayer SAM disposed on surface S decreases as less patterning material PM remains on application component AC. Consequently, the concentration of patterning material PM on self-assembled monolayer SAM disposed on surface S comprises a region of high patterning material concentration, a region of low patterning material concentration and a region of diffuse patterning concentration disposed between the regions of high and low patterning material concentration.

Altering various parameters of the method can control the amount of patterning material transferred from an application component to a surface. For example, by altering the rate at which an application component is moved over the surface, different concentrations of patterning material can be transferred to the surface. Additionally, various application component geometries can also lead to different patterning material concentrations on the surface.

V.C.3. Variation of Tip Scanning Rate, Replacement Bias and Raster Line Spacing to Form a Gradient on a Surface Bearing a SAM In one embodiment for forming a gradient in accordance with the present invention, a scanning tunneling microscopy-based substitution lithography can be employed to produce complex gradient structures by systematically varying the replacement bias and/or the lithographic scan rate and/or the raster line spacing. These gradients exhibit diffuse coverage of a gradient material (e.g., a patterning material) into the SAM at a first end of the structure, intermediate coverage through the middle, and high coverage at a second end of the pattern, which is distal from the first end. Thus, complex gradient patterns can be created and useful surface-bound gradient structures can be developed, as described herein.

Figure 3A:
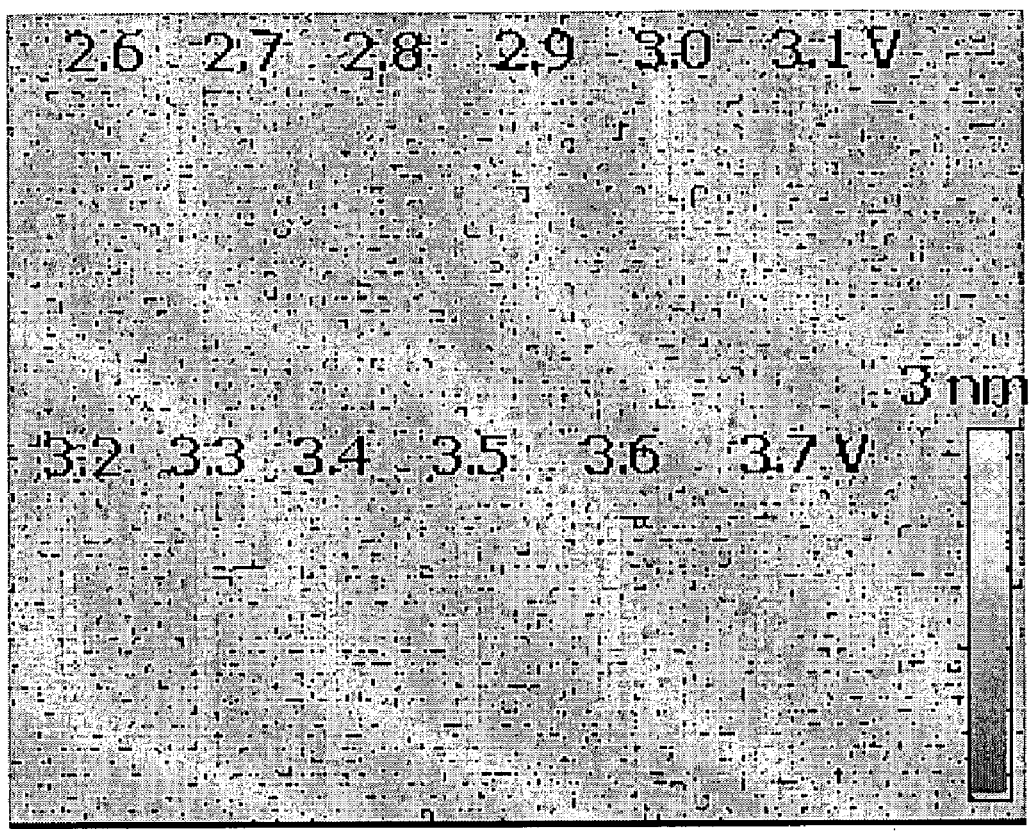
FIG. 3A depicts STM images demonstrating the efficacy of replacement of $FcC_{11}SAc$ in a $C_{12}S$-SAM as a function of replacement bias. z-scale: 3 nm.

As depicted in FIG. 3A, the lithographic scan rate (the rate at which an STM tip traverses a rastering pattern) can affect the degree to which patterning material associates with a surface, in one embodiment following and in another embodiment concurrent with, pattered desorption. The pattern depicted in FIG. 3A comprises two rows Of seven parallel lines, each 200 nm in length, and spaced 100 nm apart. In this experiment, the replacement bias (3.2 V), tunneling set point current (10 pA), and relative humidity (58%) were kept constant.

FIG. 3A depicts the observation that at low scan rate (e.g., 10 nm/s), complete substitution occurred, however the lines widths were larger than those obtained using a faster scan rate. As the scan rate is increased to a higher scan rate (e.g., 20 to 40 nm/s) optimal substitution can be achieved and ~15 nm line widths can be generated. Further increases in scan rate generally diminish the relative amount of substitution. At these increased scan rates, the patterned lines can become blotchy, appearing to leave some of the original matrix material intact within the desired pattern. At very high scan rates (>130 nm/s) the quantity of patterning material within the patterned line can be diffuse. It is likely that at very high scan rates, the tip moves at a scan rate that does not promote complete tip-induced substitution.

Thus, gradient structures can be constructed by systematically varying the lithographic scan rate, while maintaining all other STM parameters constant. For example, the 200 nm×600 nm gradient structure depicted in FIG. 3A was fabricated by holding the replacement bias (2.8 V), set point current (10 pA) and relative humidity (60%) constant. At the beginning of the formation of the structure, a scan rate of 160 nm/s initiated diffuse substitution. This scan rate was decreased incrementally in small steps (3 to 5 raster lines) by 10 nm/s, until reaching the concentrated coverage side of the pattern and a final scan rate of 20 nm/s. The average section analysis for FIG. 3A, which is shown immediately to the right of the image, shows an apparent height differential of approximately 9.9 Å (measured between arrows) between the SAM and the concentrated (brighter) side of the gradient at an imaging bias of 1.0 V.

Thus, by varying the scan rate of an STM tip over a matrix material, in the presence of a patterning material disposed in a solvent, varying degrees of incorporation of patterning material can be achieved. Specifically, different degrees of incorporation can be achieved at different locations on a surface. A gradient is, by definition, a variation in one property with respect to a second property. In the present invention, a gradient (e.g., a concentration gradient with respect to a patterning material) can be generated by varying a degree of incorporation of patterning material, which can be achieved by varying the scan rate of a STM tip over a monolayer.

Figure 3B:
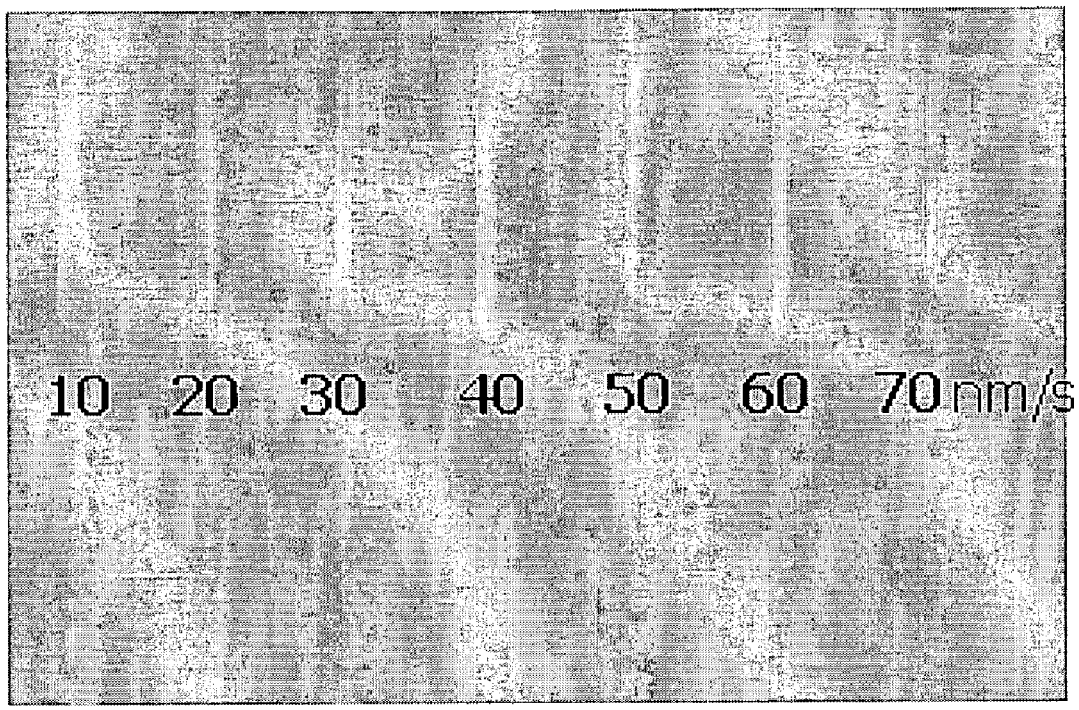
FIG. 3B depicts STM images demonstrating the efficacy of replacement of $FcC_{11}SAc$ in a $C_{12}S$-SAM as a function of replacement bias and lithographic scan rate.

A gradient can also be prepared by maintaining a constant scan rate and varying the replacement bias as the STM tip is rastered. This will have the effect of desorbing matrix material to varying degrees, which will be a function of the replacement bias. Thus, at high replacement biases, more matrix material will be removed, while at lower replacement biases, less material will be removed. By way of specific example, a 200 nm×720 nm gradient that was constructed by varying the replacement bias as disclosed herein is depicted in FIG. 3B. In preparing this gradient, the setpoint current (10 pA), lithographic scan rate (50 nm/s), and relative humidity (58%) were held constant. The gradient was constructed by beginning the rastering pattern of desorption at a replacement bias that promoted diffuse coverage (2.6 V). The replacement bias was then incrementally increased by 20 mV for every 3–5 lines drawn, arriving at the opposite end of the pattern at a bias of 3.1 V, which promoted a significant degree of substitution.

Following completion of a rastering pattern during gradient formation, an analysis can be performed to determine one or more qualities of the gradient. Continuing with the example depicted in FIG. 3B, an average section analysis is shown immediately to the right of this image. This, and related section analyses can be obtained by averaging the height values of the data within a given horizontal scan line in the region in which substitution is performed. FIG. 3B depicts an apparent height contrast differential of approximately 8.7 Å (measured between arrows) between the matrix material and the high coverage end of the gradient at an imaging bias of 1.0 V. A distinct difference in apparent height between the patterning material and the matrix material is observed in the example of FIG. 3B, due to increased transconductance through the former at this imaging bias. The gradient structure did not change in appearance over periods greater than twenty hours of continuous scanning under imaging conditions.

Summarily, a gradient structure can be fabricated by systemically varying the replacement bias, as well as the scan rate, while simultaneously varying the spacing between the lines that constitute the overall gradient pattern. Thus, gradient formation can be a function of three or more parameters. The implication of at least the disclosed parameters imparts a high degree of control over the nature of the gradient formed.

The above-described techniques can be employed to form a multidirectional gradient. That is, a gradient can be formed that is not exclusively linear and can vary in direction and configuration. Such a gradient can be formed, for example, via introduction of variation to the scan angle. Formation of such a structure can also be achieved by altering the dimensions and directions of a rastering pattern. Further, a multidimensional gradient structure can be generated by altering at least the replacement bias, the scan rate, the length of lines being substituted, and the raster line spacing within the pattern.

VI. Applications of the Present Invention

The methods and gradient structures of the present invention can play a role in a wide range of applications. For example, a gradient can be employed in the assembly of a nanoparticle-based structure and in the synthesis of organic compounds and biomolecules. These and other methods are described herein below.

VI.A. Gradient Operation

Broadly, a gradient of the present invention operates on the principle of a driving force. This driving force ushers the particle or molecule down the gradient from an area wherein the driving force is strong to an area where the driving force is weaker.

In some gradients of the present invention, the driving force associated with an area of a gradient can be varied by application of a stimulus, which can take the form of a change in the local environment of a region of the gradient. Changes in the local environment can take the form, for example, of a change in the pH, a change in the electrostatic interactions of the gradient, or a change in the relative hydrophobicity/hydrophilicity of the gradient.

Summarily, the gradients of the present invention operate on the principle of a driving force associated with the gradient, which can be employed to do work. Work can take the form of the movement of a molecule or a particle from one region of a gradient to another, for example.

VI.B. A Gradient Disposed on a Surface Adapted to Transport a Fluid or a Non-fluid Considerable work is now underway to develop microfluidic systems, particularly for performing chemical, clinical, and environmental analysis of chemical and biological specimens, among other applications. The term "microfluidic" generally refers to a system or device having a network of chambers connected by patterns having microscale dimensions, e.g., having at least-one cross sectional dimension in the range from about 0.1 μm to about 500 μm. Microfluidic substrates are often fabricated using photolithography, wet chemical etching, injection molding, embossing, and other techniques similar to those employed in the semiconductor industry. The resulting devices can be used to perform a variety of sophisticated chemical and biological analytical techniques.

Although the methods and apparatuses of the present invention are not microfluidic systems, since they are not restricted to operating on fluids and can operate on particles and molecules (which do not comprise a bulk solvent), they share many advantages that microfluidic systems offer. Microfluidic analytical systems, and those apparatuses and methods of the present invention, have a number of advantages over conventional chemical or physical laboratory techniques. For example, these systems are particularly well adapted for analyzing small samples sizes, typically making use of samples having volumes on the order of nanoliters and even picoliters. Additionally, pattern-defining substrates (i.e., a matrix material of the present invention) are ideally produced at relatively low cost, and the patterns can be arranged to perform numerous specific analytical operations, including mixing, dispensing, valving, reactions, detections, electrophoresis, and other operations. The analytical capabilities of microfluidic systems are generally enhanced by increasing the number and complexity of network patterns, reaction chambers, and the like, all of which can be achieved by employing the methods of the present invention.

A limitation of microfluidic systems, however, is the fact that the sample material must be a fluid. Since the equations of fluid mechanics generally govern the behavior of microfluidic system, such systems are typically designed around these principles. The methods and apparatuses of the present invention, however, need not be confined to the manipulation of a fluid. Indeed, the methods and apparatuses of the present invention transcend the field of microfluidics by eliminating any requirement for liquid samples. Thus, samples comprising particles can be analyzed by employing the methods and apparatuses of the present invention.

A gradient of the present invention can comprise a static gradient or a dynamic gradient. A static gradient is generally characterized as a gradient in which the driving force associated with the gradient, which can be a function of the concentration of a patterning material disposed on a surface, remains constant at any given time at any given point on the gradient. For example, a static gradient can comprise a region of high driving force, a region of low driving force, and a region of intermediate driving force. At any given point in time, the driving force associated with a given region of the gradient remains constant. A dynamic gradient, on the other hand, can comprise the same regions of driving force as a static gradient. However, in a dynamic gradient, the driving force associated with a given point on a dynamic gradient can be altered by the application of an external stimulus after the gradient structure has been formed or fabricated. As disclosed herein below, an interaction can take a variety of forms including, but not limited to application of a current, alteration of pH conditions, or even transient chemical modification of the gradient material.

As described, a gradient of the present invention can be static or dynamic. Once a particle enters the influence of a static gradient, it is transported in one direction only due to the fixed relationship of the driving force associated with the various regions of the static gradient. In the dynamic gradients of the present invention, however, the motion of particles within a dynamic gradient is a function of the energy map of the gradient (i.e., the driving force at a given point in time, at a given point on the gradient). Dynamic gradients can be switched on and off or reversed in direction, allowing for transport in either direction along the gradient. The controllably variable interaction force between the surface and a transported molecule or particle can, for example, facilitate tight binding, which prevents movement of a transported particle or molecule and, alternatively, loose binding, where a transported particle or molecule is free to travel and finally released. The gradients and patterns can be configured such that a particle or molecule is not released from the pattern containing a gradient until desired.

In one embodiment, both static and dynamic gradients are constructed in the space of a desorbed pattern, i.e. a region in which matrix material disposed on a surface is desorbed. However, this is not a requirement. The combination of a desorbed pattern and a patterning material disposed on the region from which matrix material is desorbed can define the path or paths (since a gradient of the present invention can be multidirectional) that a transported particle or molecule will follow.

In one embodiment, a gradient is characterized as a chemically-defined structure rather than a topographically-defined structure. By way of non-limiting example, a gradient can comprise a line of positively-charged patterning material disposed on a surface, surrounded by negatively-charged matrix material, which is also disposed on the surface. In another embodiment, a hydrophilic patterning material surrounded by hydrophobic matrix material can define the gradient. In yet another embodiment, a matrix material can be polymeric and can present a steric barrier to particle motion outside the a region of patterning material disposed in a region in which matrix material has been desorbed and patterning material substituted therefor. The desorbed pattern-formation technique employed (such as those described herein) and the particle diameter can play a role in determining the width of a pattern.

VI.B.1. Static Gradient

An example of a static chemical gradient comprising a patterning material that has been substituted for desorbed matrix material is depicted in FIG. 4. At a first end of the gradient depicted in the figure, one chemical species predominates, while at a second end of the gradient, which is distal from the first end, the other chemical species predominates (depicted in FIG. 4 as brighter/taller in the STM image). This type of gradient can facilitate the transport of a molecule or particle from the first end of such a gradient to the second end.

In one embodiment, one component of a gradient is hydrophobic (e.g. $-S(CH_2)_nCH_3$, where in one embodiment n is any integer, in another embodiment any integer from 1 to 50, and in yet another embodiment n is 1, 2, 3, 4, 5, 6, 7, 8, 9, 10, 11, 12, 13, 14, 15, 16, 17, 18, 19 or 20), which can be a patterning material disposed on a surface, and another is hydrophilic (e.g. $-S(CH_2)_nCO_2H$, where in one embodiment n is any integer, in another embodiment any integer from 1 to 50, and in yet another embodiment n is 1, 2, 3, 4, 5, 6, 7, 8, 9, 10, 11, 12, 13, 14, 15, 16, 17, 18, 19 or 20), which can be matrix material disposed on a surface that has been incompletely desorbed from a region. In this example, a particle or molecule comprising a hydrophilic surface that is placed on the hydrophobic end of the gradient will spontaneously travel along it to the progressively more hydrophilic side. Conversely, a particle or molecule comprising a hydrophobic surface that is placed on the hydrophilic end of the gradient will travel along the gradient to the progressively more hydrophobic side. This phenomenon has been demonstrated with drops of water that "run uphill" in the presence of a chemical gradient (see, e.g., Chaudhury & Whitesides, (1992) Science 256: 1539), but has not been demonstrated with non-fluids, prior to the disclosure of the present invention. Thus, molecular interactions can drive the motion of particles and molecules.

Unlike the work of Chaudhury & Whitesides and other researchers in the field, the present invention discloses apparatus and methods adapted to drive the motion of particles and molecules. This concept is different from that of prior art research because particles and molecules are not the equivalent of bulk fluids. Thus, while the present invention discloses: employing a driving force to direct motion, it is directed to driving the motion of particles and molecules, rather than bulk solvent, making it a leap beyond what is now known in the art. Prior art methods have not addressed or solved this problem.

A gradient can be premised on a variety of physical phenomena, not just hydrophilicity and hydrophobicity, and can be designed and fabricated by the methods of the present invention. Virtually any physical phenomenon can form the basis of a gradient. For example, a gradient can be formed that is premised on electrostatics. In a gradient based on electrostatics, the gradient can comprise compounds comprising the chemical species $S(CH_2)_nNMe_3^+$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19 or 20), which can be a patterning material disposed on a surface, and $S(CH_2)_nSO_3^-$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19, or 20), which can be matrix material disposed on a surface that has been incompletely desorbed, with each species predominating in concentration in regions distal to one another. In this type of gradient, a negatively charged transported molecule or particle disposed on a region comprising a high concentration of $S(CH_2)_nSO_3^-$ will migrate to a region of higher $S(CH_2)_nNMe_3^+$ concentration, while a positively charged transported molecule or particle disposed on a region comprising a high concentration of $S(CH_2)_nNMe_3^+$ will migrate to a region of high $S(CH_2)_nSO_3^-$ concentration.

In yet another embodiment of the present invention, a gradient can be premised on hydrogen bonding between a particle or molecule and a gradient material. In a gradient based on hydrogen bonding, the gradient can comprise the chemical species $S(CH_2)_nCH_3$ (where in one embodiment n is any integer, in another embodiment any integer from 1 to 50, and in yet another embodiment n is 1, 2, 3, 4, 5, 6, 7, 8, 9, 10, 11, 12, 13, 14, 15, 16, 17, 18, 19 or 20), which can be patterning material disposed on a surface, and $S(CH_2)_nOH$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19 or 20), Which can be matrix material disposed on a surface that has been incompletely desorbed, with each species predominating in concentration in regions distal to one another. In this type of gradient, a transported molecule or particle adapted to form hydrogen bonds that is disposed on a region comprising a high concentration of $S(CH_2)_nCH_3$ will migrate to a region of higher $S(CH_2)_nOH$ concentration, while a transported molecule or particle not adapted to form significant hydrogen bonds that is disposed on a region comprising a high concentration of $S(CH_2)_nOH$ will migrate to a region of $S(CH_2)_nCH_3$ concentration.

In yet a further embodiment, a gradient can be premised on the acidity or basicity of a particle or transported molecule or particle relative to a gradient material. In a gradient based on acidity, the gradient can comprise $S(CH_2)_nCO_2H$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19 or 20), which can be a patterning material disposed on a surface, and $S(CH_2)_nSO_3^-$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19 or 20), which can be matrix material disposed on a surface that has been incompletely desorbed, with each species predominating in concentration in regions distal to one another. In this type of gradient, a transported molecule or particle that is relatively acidic that is disposed on a region comprising a high concentration of $S(CH_2)_nCO_2H$ will migrate to a region of higher $S(CH_2)_nSO_3^-$ concentration, while a transported molecule or particle that is more basic that is disposed on a region comprising a high concentration of $S(CH_2)_nSO_3^-$, will migrate to a region of $S(CH_2)_nCO_2H$ concentration. Broadly, a gradient premised on the acidity or alkalinity of the gradient material can comprise species that comprise head groups that have different $pK_a$ values.

In practice, an appropriately functionalized particle or molecule can be placed in contact with this gradient and will migrate toward one region of the gradient. For example, a positively charged transported molecule or particle will move towards the negatively charged side of a gradient, or a transported molecule or particle with basic groups will move towards the most acidic side of a gradient.

In one embodiment, a static gradient is adapted to transport a fluid or a non-fluid and comprises a surface. A surface can comprise any surface adapted for attachment of a matrix material and patterning material. Surfaces include, but are not limited to gold and ITO.

A static gradient comprises a matrix material disposed on the surface. Any material can serve as a matrix material. In one embodiment, a matrix material comprises a binding group adapted to facilitate association of the matrix material with the surface and a head group. In one embodiment, if a surface comprises gold, a matrix material can comprise a thiolate binding group, which can facilitate association of the matrix material with the surface. The head group can comprise any functional group and can be selected based on a desired property of the gradient.

Additionally, a static gradient comprises a patterning material disposed on the surface and in contact with the matrix material. In one embodiment, the patterning material is disposed on the surface so as to define various regions of concentration. In another embodiment, patterning material is disposed so as to form a first region comprising less than or equal to about 75% patterning material, a second region comprising less than or equal to about 25% patterning material, and a third region comprising less than about 75% patterning material, but patterning material more than about 25%, the third region being contiguous with the first and second regions. Representative patterning materials are discussed herein above. However, selection of a patterning material will be dependent, in part, on the nature of the particle or molecule that is being transported along the gradient. It is noted that in the context of a concentration of patterning material, the descriptor "low" is relative to the concentration of patterning material comprising the region of high patterning material. A region of low patterning material concentration can also comprise a region of high concentration of a second patterning material. That is, a region of a gradient can comprise an area of two or more patterning materials.

A static gradient exhibits the property that the potential energy contained in the matrix material at a given point on the gradient remains constant. Thus, a given transported particle or molecule disposed at a given point on a static gradient will always behave in the same way and, unlike a dynamic gradient, that behavior cannot be altered. For example, a hydrophobic transported molecule or particle placed in a hydrophilic region of a gradient comprising a hydrophilic region and a hydrophobic region will be always be transported to the region of lower hydrophilicity, and the gradient cannot be adapted to alter this behavior.

VI.B.2. Dynamic Gradient

In another aspect of the present invention, a dynamic gradient is disclosed. A unique property of a dynamic gradient is the ability to manipulate the motion of a molecule or particle disposed on the gradient. This ability is provided, in part, by the ability to alter the driving force in a region of a gradient by altering the local environment of the region. For example, in a dynamic gradient, if a transported particle or molecule is traveling along a gradient and the chemical (or other) environment around the transported molecule or particle is altered, the motion of the transported molecule or particle can be made to stop or even reverse. This idea forms the basis of a dynamic gradient, as discussed below.

In one embodiment, a dynamic gradient is premised on electrostatics. For example, a gradient comprising a high concentration of $-S(CH_2)_nNH_2$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19 or 20) in a first region that gradually decreases in concentration with the length of the gradient, and a high concentration of $-S(CH_2)_nCO_2H$ (where in one embodiment n is any integer, in another embodiment any integer from 1 to 50, and in still another embodiment n is 1, 2, 3, 4, 5, 6, 7, 8, 9, 10, 11, 12, 13, 14, 15, 16, 17, 18, 19 or 20) in a second region distal to the first region which decreases in concentration with the length of the gradient can be constructed using techniques described above. In this embodiment, in a low pH aqueous environment, the gradient will run from positively charged to neutral (e.g., $-S(CH_2)_nNH_3^+$ to $-S(CH_2)_nCO_2H$). Conversely, in a high pH aqueous environment, the gradient will run from neutral to negatively charged (e.g., $-S(CH_2)_nNH_2$ to $-S(CH_2)_nCO_2^-$). A charged transported molecule or particle comprising non-pH sensitive groups (e.g., $-S(CH_2)_nNMe_3^+$) will travel at substantially different speeds under low pH and high pH environments because the chemical driving force of the gradient is altered by the change in pH. By employing techniques for characterizing particle velocity described herein, velocity versus pH profiles can also be determined.

For many applications, it is desirable that a gradient is completely reversible. That is, it is sometimes preferable that a gradient has the ability to transport a transported molecule or particle in more than one direction. This can be accomplished by employing a gradient comprising, for example, $-SC(CH_3)_2(CH_2)_nSO_3H$ (which is present in high concentration at a first end of the gradient) and $-S(CH_2)_nCO_2H$ (which is present at a second end of the gradient). These two species are present in approximately equal concentrations at a midpoint between the ends of a gradient.

The $pK_a$ of the sulfonic acid group, which is about 1, is significantly below that of the carboxylic acid group, which is about 4.5 (both of these are about 2–3 $pK_a$ units higher when bound on the surface as compared to in solution). The two methyl side groups added next to the thiol group reduce the potential aerial density of sulfonic acid groups as compared to carboxylic acid groups. The result is a gradient with a compositional variation going from a lower density of sulfonic acid groups at one end to a higher density of carboxylic acid groups at the other end.

At a high pH well above the $pK_a$ of both species, both species will be deprotonated, and the result is a gradient running from a lower negative charge density at the sulfonate rich end to a higher charge density at the carboxylate rich end. At a pH below the $pK_a$ of the carboxylic acid group, but above that of the sulfonic acid group, the gradient of charge is reversed. This pH results in a gradient running from a negative charge density at the sulfate rich end to virtually no net charge density at the carboxylate rich end. At a low enough of a pH, neither end would be charged, and the charged particle would be released. This last step is important, since it allows for the release of a particle or molecule after a desired operation has been accomplished. The relative $pK_a$ values of the different, acidic head groups can be tuned structurally as necessary. A dynamic gradient can be employed in many of the applications discussed herein below.

In one embodiment, a dynamic gradient disposed on a surface is adapted to transport a fluid or a non-fluid. The surface can comprise any material. In one embodiment, the surface comprises gold, and in another embodiment, ITO. A dynamic gradient can also comprise a SAM comprising matrix material disposed on the surface. A matrix material can comprise any material, with the caveat that the matrix material preferably comprises a binding group that facilitates association of the matrix material with the surface and a head group, which imparts a chemical property to the matrix material. As with a matrix material of any of the methods of the present invention, the dimensions of a matrix material can vary. That is, the material comprising a matrix material can vary in length and overall structure. For example, if it is desired to prepare a SAM that can form a deep pattern (as measured from the surface to the head group of a matrix material) when matrix material is desorbed, it might be desirable to select a matrix material comprising a straight chain moiety comprising a plurality of carbon-carbon single bonds, such as dodecane derivatized with a thiol group. When a more shallow pattern (as measured from the surface to the head group of a matrix material) is desired, a compound comprising a fewer number of carbon-carbon single bonds or a number of carbon-carbon double bonds can be selected. Again, this matrix material can comprise a binding group and a head group.

In one embodiment, a dynamic gradient comprises a patterning material disposed on the surface and in contact with matrix material, which is adapted to vary in driving force in response to a stimulus. That is, the patterning material can be adapted to exhibit different properties in response to a change in the local environment at various points on the gradient. As discussed above, a change in the local environment can comprise a change in pH, hydrophobicity, etc. By altering the local environment of a portion or all of a patterning material, it is possible to influence the effect of the gradient on a particle or molecule associated with the patterning material. Thus, the driving force associated with a region of a dynamic gradient can be altered, and the path and/or direction of a molecule or particle associated with the patterning material altered as well.

VI.B.3. Characterization of a Gradient

Regardless of whether a gradient is a static gradient or a dynamic gradient, it can be conveniently characterized, for example, by a combination of near-field scanning optical microscopy (NSOM), lateral force microscopy, and fluorescence microscopy with CCD detection. Selection of a precise combination of techniques can depend on the size scale of the desorbed pattern and/or the dimensions of the gradient. For example, nanoscale gradients and patterns can be conveniently characterized with lateral force microscopy (LFM). LFM detects friction force differences between chemically distinct surface-bound molecules and the tip. For example, friction force differences between methyl- and carboxylic acid-terminated thiols are detected routinely with 10 nm resolution; LFM can be extended to all of the nanometer-scale gradients of the present invention.

Gradients formed on the hundreds of nanometers to several microns scale can be characterized with fluorescence microscopy. Fluorescence microscopy is well suited to the determination of transported molecule and particle diffusion and directed motion using various machine strategies. For example, the probability density for a particle can be determined by making a number of measurements of the location of a single fluorescent nanometer scale (5–200 nm) particle on a surface that is 20 $\mu$m×20 $\mu$m. The resolution of a fluorescence microscope is approximately 1 $\mu$m, so the motion of a transported molecule or particle in a grid of that size comprises 400 points.

The stochastic motion of a particle can be determined in a substrate layer comprising a single type of organic molecule (e.g., alkane thiols terminated with hydroxy, amine, carboxy groups, etc.). Directed motion along a gradient can also be determined for comparison on a mixed monolayer substrate.

VI.B.4. Characterization of a Transported Molecule or Particle in the Presence and Absence of a Gradient Prior to the formation of a gradient, it might be desirable to characterize a transported molecule or particle's behavior in the absence of a gradient. This process can be advantageous for molecule or particle design, as well as for predicting how the molecule or particle will behave when applied to a gradient of the present invention. Additionally, it might be beneficial to be able to characterize the behavior of a particle or molecule in the presence of a gradient. This ability can be of assistance in particle and molecule design, as well as in gradient design. The present section, therefore, discloses representative methods of characterizing a molecule or particle before it is applied to a gradient, as well as while the molecule or particle is in contact With a gradient.

Figure 6:
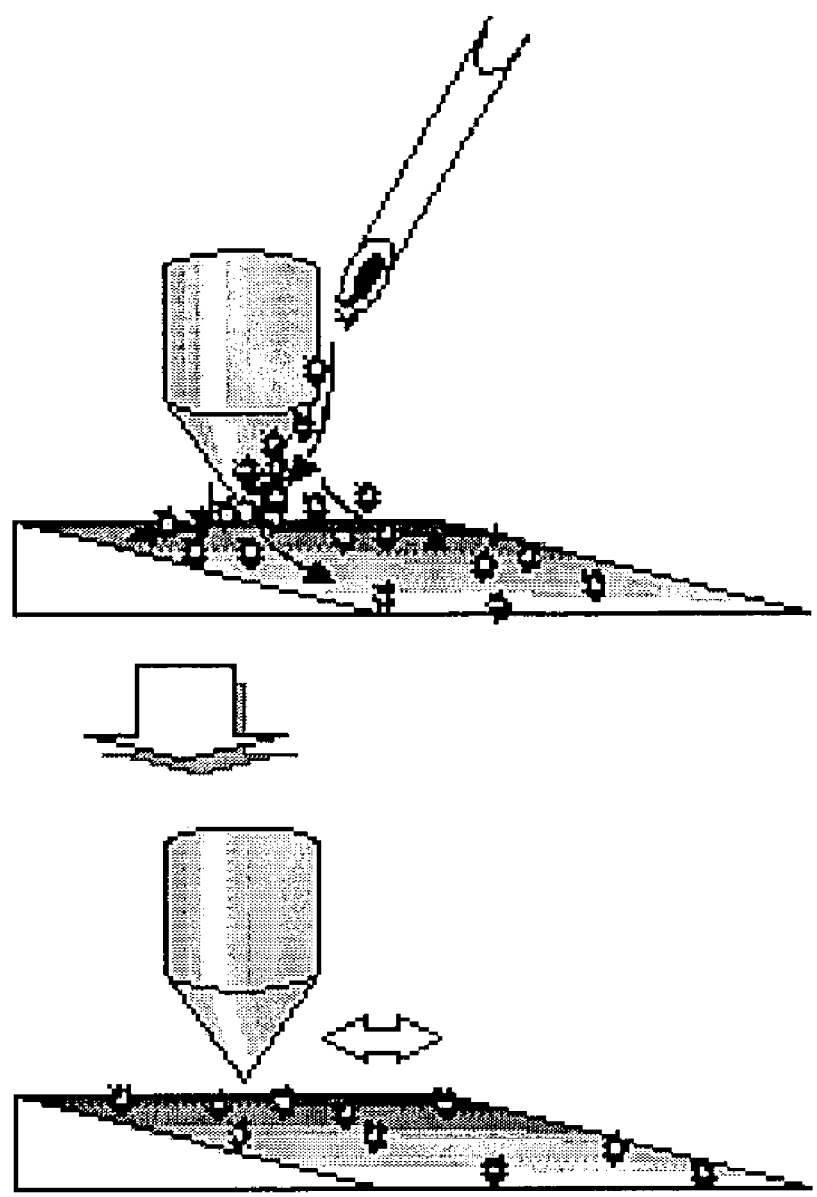
FIG. 6 is a schematic diagram depicting one approach for introducing nanoparticles at the top of a gradient.

FIG. 6 is a schematic diagram describing one approach, in accordance with the present invention, for characterizing the interaction between a gradient and a particle, in this case, a nanoparticle (although a particle can also be a molecule or a particle of other dimensions). In the approach depicted in FIG. 6, a quantity of nanoparticles is placed on a gradient. Although any approach to introducing nanoparticles or microparticles to a gradient can be employed, a cannula is depicted in FIG. 6. Once in contact with the gradient, the particles are free to disperse. Subsequently, the surface can be imaged by STM. This approach can be employed to characterize the effect of a gradient of any composition on particles and molecules of any composition. This method can offer insight into the nature of a gradient and can reveal the presence of phase separation.

When selecting and/or designing a molecule or particle for transport along a gradient of the present invention, it is desirable to determine the rate of diffusion of the particle in two dimensions in the absence of a gradient. When the unperturbed, thermally-activated rate of diffusion is known, it is easier to determine the effects of a gradient on transport. Thus, one can measure the rate of diffusion of a candidate molecule and/or particle such as macromolecules, microparticles, nanoparticles, and large colloidal objects confined to surfaces in the absence of a gradient.

Determining the rate of diffusion of objects on the order of 250 nm or greater can be readily achieved. In one approach, the movement of a single molecule or particle can be tracked as the molecule or particle performs a random walk. This can be achieved by employing an optical microscope equipped with a digital camera. Automating the determination of the particle's center of mass as a function of time can be achieved by employing computer software known in the art. If the particles or molecules are fluorescent, for example, the detection limit becomes much smaller. In this approach, the surface density of the particles can be low enough that it can be approximated that each fluorescing point is a single particle. Given that the spatial resolution of an optical microscope is about 250 nm, this approximation can be made, for example, when no more than one particle is present over an area of about 1 $\mu m^2$. The methods of the present invention allow for dosing the surface with an arbitrary number of particles, which does not present any difficulty for these methods. When characterizing a gradient, a molecule or particle can be introduced to the gradient by following the protocol depicted in FIG. 6.

Near-field scanning optical microscopy (NSOM) is another exemplary technique that can be employed in the characterization of a molecule or particle in the presence or absence of a gradient. NSOM is an exceptionally powerful high-resolution optical technique that can be employed in the direct topographic imaging of nanoscale features. NSOM can also spatially locate fluorescent signals to within about 50 nm. These characteristics make NSOM highly useful for characterization of particles and molecules in the presence or absence of a gradient, when it is desirable to determine the three-dimensional size and spatial location of the individual particles or molecules, as well as the product of the assembly of the particles or molecules.

The NSOM technique can be used to examine a particle or molecule that is disposed on a gradient. This technique is useful, in part, because although the NSOM tip is always in close contact with the surface, it scans over the entire surface and, therefore, the tip actually only spends a very short time at any one point. Thus, as long as the interaction of the tip with a molecule or particle is small, the integrated impact of the tip on the gradient (or a molecular machine of the present invention) is not significant. Although NSOM is slower than other direct optical imaging techniques, its ability to generate high-resolution three-dimensional images makes it a favored technique for the characterization of a molecule or particle disposed on a surface.

VI.B.5. Characterizing a Transportation Rate and/or Velocity

With respect to a molecular machine of the present invention, efficient machine operation requires that particles be transported from one region to another region. For example, when a molecular machine is disposed on a microchip, transportation can occur between a first on-chip region to a second on-chip region. For a molecular machine, simple diffusive transport is too slow to be effective, and can be stochastic in nature. Gradients, on the other hand, facilitate transport of molecules and particles under defined, non-stochastic conditions. Thus, it is useful to understand and be able characterize not only the gradient, but also its effect on molecule and particle movement. This goal can be accomplished via several different techniques, such as those discussed below.

One technique for gradient characterization is a simple extension of the direct imaging approach described herein above. Particles can be dosed randomly on a surface embodying a gradient. Then, the particle motion is tracked, using any of the techniques described herein. If a gradient is a static gradient, the tracking of the molecules or particles is complete when all of the particles reach an endpoint of the gradient region. In the case of a dynamic gradient, the variable parameters associated with a dynamic gradient can be modulated, and the effect of the modulation on particle motion can be determined. As described, the direct observation approach is applicable for large particles, fluorescent micro- or nanoparticles, metallic micro- or nanoparticles, and fluorescently labeled polymers. Tracking is complete when the molecules or particles reach a desired position.

In the gradient characterization methods and in the operation of a gradient of the present invention, a strategy for introducing nanoparticles or microparticles at the top of a gradient can be employed. One method of introducing molecules or particles to a gradient is disclosed in FIG. 6. It is not necessary that particles be deposited in only one region of the gradient to visualize their transport characteristics. However, this technique can be employed as a "jump start" for beginning the operation of a molecular machine of the present invention.

In another method of introducing molecules or particles to a gradient, "wicking" of particles onto a scanning probe tip can be employed for site-directed delivery of a particle or molecule. By rinsing the majority of the particles away, this method can be employed to dispose a small number of molecules or particles on a gradient. By employing non-contact mode atomic force microscopy (AFM), a method that is known in the art, particle and molecular motion on a gradient can be observed and characterized by employing this non-perturbative probe technique. Additionally, "phase mode" imaging can be employed to image surfaces where the AFM tip is resonating about several nanometers above the surface. Under these conditions, long-range forces can provide sufficient contrast so that the AFM tip can actually image the particles without perturbing them at all.

VI.C. Molecular Machines

Microelectromechanical systems (MEMS) are an area of intense research. These systems involve the fabrication of micro-scale structures prepared from silicon, or occasionally from other materials such as gallium arsenide, metals, glasses, ceramics, or plastics, by typical integrated circuit industry microfabrication techniques (such as photolithography) or additive/subtractive processes (such as deposition and etching). While interesting systems have been developed, these systems are complicated and limited in application and construction. Thus, it is desirable to simplify and increase the versatility of these systems. The present invention fills this need by disclosing molecular machines, which comprise the gradients of the present invention, that can be employed in a variety of applications, including, but not limited to assembling a nanoparticle heterostructure, assembling a nanoparticle, and performing chemical reactions on a chip. These and other molecular machines are disclosed and described in the following sections.

VI.C.1. Molecular Machine for Assembling a Nanoparticle Heterostructure

A molecular machine, such as a "molecular assembly line" described herein, is well suited for nanoscale manufacturing projects in which the sequence and dimensionality of products must be controlled precisely. These criteria are particularly important in electronics. Microelectronic devices rely on metal-insulator-metal (MIM), metal-insulator-semiconductor (MIS), and metal-semiconductor (MS) sequences, for example. Quantum well lasers and resonant tunnel diodes also employ perfectly repeating high and low bandgap materials.

A particle assembly line as described herein offers many advantages for nanostructure fabrication. First, it is scaleable; three or more particles can be organized in a desired sequence. Second, one or more of the particles can be programmed to bind to other nanostructures fabricated on a different assembly line located on the same chip. Additionally, the "molecular assembly line" concept can form the basis for more complicated strategies. It is noted that although nanoparticles are specifically enumerated in the molecular machine applications of the present invention, microparticles and particles having larger or smaller dimensions can also be employed in the molecular machines of the present invention. Thus, the terms particle and nanoparticles specifically encompass microparticles and particles having dimensions smaller and larger than nanoparticles. Complex molecules can also be assembled by employing the methods of the present invention.

In one embodiment, a molecular machine for assembling a nanoparticle heterostructure comprises two or more reservoirs, each reservoir comprising a quantity of nanoparticles. A reservoir can comprise a structure fabricated by desorption of matrix material disposed on a surface or can be a physical depression or similar structure disposed on a surface. A representative surface for a molecular machine of the present invention comprises a microchip; however, a surface need not comprise a microchip and suitable surfaces can be selected, in part, based on the nature of a nanoparticle disposed in the reservoir.

A nanoparticle complex can comprise almost any material including, but not limited to metals, metal oxides, conductive polymers, and semiconductors. Metals and metal oxides suitable for use in the present invention include, but are not limited to titanium, titanium dioxide, tin, tin oxide, silicon, silicon dioxide, iron, iron$^{III}$ oxide, silver, gold, copper, nickel, aluminum, steel, indium, indium tin oxide, fluoride-doped tin, ruthenium oxide, germanium cadmium selenide, cadmium sulfide, and titanium alloy. Gold and tin oxide ($TiO_2$) are especially useful due to their well-characterized reactivity and electrochemical profiles.

Particles comprising the above materials and having diameters less than about 1,000 nanometers are available commercially or they can be produced using $HAuCl_4$ and a citrate-reducing agent or other reactants using methods known in the art. See, e.g., Marinakos et al., (1999) *Adv. Mater.* 11:34; Marinakos et al., (1998) *Chem. Mater.* 10:1214–19; Enustun & Turkevich, (1963) *J. Am. Chem. Soc.* 85:3317. Various physical and chemical vapor deposition processes, such as sputter deposition, can be also used. See, e.g., Hayashi, (1987) *J. Vac. Sci. Technol.* A5(4): 1375–84; Hayashi, (1987) *Physics Today*, December 1987, 44–60; *MRS Bulletin*, January 1990, pgs. 16–47. Tin oxide nanoparticles having a dispersed (in $H_2O$) aggregate particle size of about 140 nanometers are available commercially from Vacuum Metallurgical Co., Ltd., Chiba, Japan. Other commercially available nanoparticles having the desired composition and size range are available, for example, from Vector Laboratories, Inc., Burlingame, Calif., United States of America.

Another consideration when selecting a material for a nanoparticle is the chemical reactivity profile of the material. The chemical reactivity profile of a material is a consideration, because other entities can be associated with the nanoparticle. Additionally, it might be desirable to associate a secondary association component (e.g. biotin or avidin) with a nanoparticle. Therefore, the reactivity of a nanoparticle to a desired association component can also be a consideration. Thus, considerations when selecting and/or designing a nanoparticle include, but are not limited to size, material, chemical reactivity of the material, and the ease with which a given chemical component can associate with the nanoparticle.

In one embodiment, a nanoparticle of the present invention can be adapted to associate with another nanoparticle. This can be achieved, for example, by associating an association moiety with the nanoparticle. In the example described herein above, avidin and biotin are independently associated with different population of nanoparticles, however the present invention is not limited to the use of these two molecules. Indeed, any molecules known to associate with one another can be employed as association moieties.

Any molecules or structures exhibiting an inherent affinity for each other can be employed as association moieties. In practice, each population of nanoparticles (i.e., a population of nanoparticles comprising biotin and a population comprising avidin) is disposed in separate reservoirs and is not exposed to each other until the nanoparticles meet in a region of a pattern where association can take place. Thus, each population of nanoparticles can be prepared separately and this separation can be maintained until members of the two populations are exposed to each other in the region of a pattern where association can take place (hereinafter a "reaction region"). Any pair of (or even three or more) moieties can be employed as an association moiety, with the caveat that the moieties exhibit a known or suspected affinity for each other.

A molecular machine adapted for assembling a nanoparticle heterostructure also comprises two or more independently operable gate structures in communication with the two or more reservoirs and a reaction region. A reaction region can comprise a region formed by desorption of matrix material and substitution of a patterning material, per the methods disclosed herein. In one embodiment, a reaction region can be lined with chemical moieties that can direct a molecule or particle released from a reservoir to a region of the reaction region, such as a central region of the reaction region. In one embodiment, a reaction region is maintained under conditions optimal for heterostructure formation (e.g., optimal pH, electrostatic conditions, etc.).

Gate structures can be controlled, in one embodiment, by voltage. In this embodiment, a gate structure can comprise an element that assumes an open or closed conformation in response to a bias applied across the gate. Molecular gate structures are known in the art and can be employed in the present invention. The selection of a given gate structure can be based, in part, on the scale of the molecular machine. For example, when the scale of a molecular machine comprises microscale dimensions, physical gates, which operate primarily on the basis of steric interaction, can be employed. When the scale of a molecular machine comprises nanoscale dimensions, a gate structure comprising one or more molecules that operate primarily on the basis of molecular interactions (e.g., electrostatic repulsion, van der Waal's interactions, etc.) can be employed. Stimulating molecules can also be employed to affect the properties of a gate.

Alternatively or in addition, a nanoparticle heterostructure assembly machine comprises two or more dynamic gradient tracks, each in communication with an independently operable gate structure and the reaction region, the two or more dynamic gradient tracks comprising one or more regions of variable potential energy. The two or more dynamic gradient tracks can be formed as described herein.

By the definition of a dynamic gradient track, as opposed to a static gradient track, the dynamic gradient tracks of a nanoparticle heterostructure assembly machine can exhibit different properties under different conditions. This can be achieved because a dynamic gradient track of the present invention can comprise one or more regions of variable driving force. In the context of the present invention, variable driving force describes the force available to drive the motion of a particle or structure under certain conditions, or in response to a stimulus. Thus, the driving force associated with a given region of a dynamic track can vary regions of high driving force and low driving force. The driving force can be employed to transport a particle or molecule along a gradient, or to hold the particle or molecule in place. Thus, a nanoparticle disposed on a dynamic gradient track can be induced, for example, to change direction, to stay in a fixed location, or to travel to a certain point along the gradient track. This ability can be employed in directing a nanoparticle to a reaction region and sequentially assembling a nanoparticle heterostructure.

Figure 7:
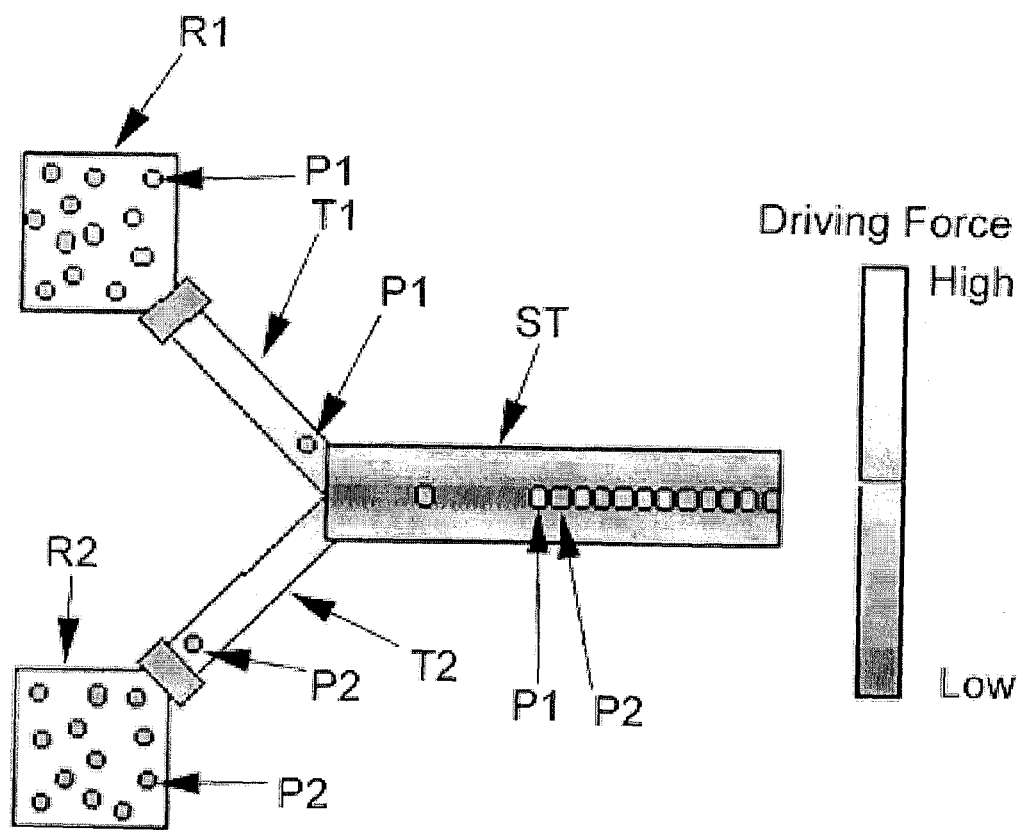
FIG. 7 is a schematic diagram depicting an embodiment of a molecular machine adapted to assemble nanoparticle heterostructures.

The gradients and transportation principles of the present invention can be employed in the manufacture of one-dimensional nanoparticle heterostructures (e.g., nanoparticle structures comprising alternating gold and cadmium selenide (CdSe) nanoparticles). These structures can be employed, for example, as nanoscale analogues of MIS junctions. By way of specific example, an alternating one-dimensional chain of gold and CdSe particles can be assembled as depicted in FIG. 7. In this example, CdSe particles P1 capped with both mercaptoalkyl-amines and biotinylated alkylthiols are placed in one reservoir R1, while gold particles P2 capped with mercaptoalkylamines and avidin in another reservoir R2. Two carboxlate-terminated thiol dynamic gradient tracks T1 and T2 are then formed by patterned desorption of matrix material from a surface and substitution of patterning material for the desorbed matrix material. Tracks T1 and T2 lead away from reservoirs R1 and R2 and merge to form a single track ST, which itself can be a gradient. Gates on reservoirs R1 and R2 can be opened and closed repeatedly to release, preferably, a single particle of each type. Both particle types are adapted to move down their respective tracks T1 and T2 and into single track ST. In one embodiment, single track ST in which the particles meet is of the same thickness as the particle diameter, thus facilitating the formation of one-dimensional particle chains as depicted in FIG. 7.

In this example, the affinities of biotin for avidin and avidin for biotin provide a driving force and drives particle linking. For a given association, an optimum gate frequency for releasing a single particle through the gate can be employed. However, it is possible that on any given cycle more than one particle is released into the reaction region. In this example, if two gold or CdSe particles that independently comprise biotin and avidin end up next to each other, they will not bind covalently. This is due to the low affinity of biotin and avidin for themselves. Thus it is possible to "anneal" out such defects by disrupting their hydrogen bond interactions with the substrate (via slight solution dielectric changes, for example). The remainder of the one-dimensional chain can then migrate to fill in the void left after removing the defective particle.

The disclosed machine can be employed to assemble a nanoparticle heterostructure. Such a heterostructure can form the basis of an electronic device, and can form a component of, for example, a nanoscale analog of a MIS junction or another electronic component.

Nanoparticle heterostructures formed by employing the molecular machines of the present invention can also be employed as unique identifiers. A given population of assembled nanoparticle heterostructures can comprise a population of structures that are structurally unlike any other population of nanoparticle heterostructures. These structure differences can facilitate the identification of a member of this population of heterostructures that is present in a combination of structures.

A molecular machine of the present invention can assemble such structures. For example, a heterostructure can be assembled that comprises a plurality of segments of different sizes (or other detectable property) oriented next to each other, much like a bar code. Various heterostructure components can be joined in a specific and, in one embodiment, identifiable order to form a unique heterostructure. By way of example, a heterostructure can be formed by a molecular machine of the present invention and can comprise two or more components sequentially associated with each other in a desired order. In one embodiment, the heterostructure is formed so as to be detectable by employing available methodologies.

In one embodiment, the heterostructure is configured so as to facilitate association of a probe moiety to the heterostructure itself. A probe moiety can comprise any structure. A non-inclusive but representative list of suitable probe moieties includes, for example, nucleic acids, proteins, antibodies and antibody fragments, biotin, avidin, various biological compounds, hydrophilic compounds, hydrophobic compounds, acidic compounds, basic compounds, electroactive compounds or any compound known or suspected of having an affinity for another compound.

When a probe moiety is associated with a heterostructure, the heterostructure can be used in a high throughput screening method. In this application, the heterostructure can be incubated with a mixture to be screened for the presence of a target compound. In one embodiment, the incubation is under conditions suitable for the association of the probe moiety with the target compound. After a desired incubation period, the presence of a complex comprising the probe moiety (and thus the heterostructure) and the target compound is detected. The detection can be based on any of a variety of available detection methods.

In another embodiment, a plurality of different heterostructures, each with a different probe moiety associated therewith, can be incubated with a mixture. Again, heterostructure-target compound multimers are allowed to form under appropriate conditions. Then, the presence of heterostructure-target compound complexes is detected.

An advantage of employing heterostructures in these applications is the ability to uniquely identify each heterostructure based on its composition. Such an identification can be analogized to reading a bar code. The unique identification of the presence of a heterostructure can be ascertained by methods commensurate with the composition of the heterostructure, but can comprise optical-based methodologies, such as laser-based methods. By identifying first, that a complex has formed, and second, the nature of the probe moiety that associated with the target compound, a mixture can be rapidly screened for the presence of a given target compound.

Those of skill in the art will recognize that additional steps can be performed in the above applications. For example, the additional step of removing non-binding heterostructures can be performed. Additional steps can also be performed to associate a probe moiety with a heterostructure.

In another application, a heterostructure formed by a molecular machine of the present invention can be employed as an identifier associated with another structure. The relatively small size of a heterostructure facilitates the labeling of a wide range of structures. Conceivably, structures as small as cells can be labeled with a heterostructure, thus enabling subsequent identification of the cell, regardless of its local environment. Or, a given compound can be associated with a heterostructure and the localization of the compound in a system can be ascertained via identification of the presence of a heterostructure.

This non-inclusive list of applications discloses the range of applications for a heterostructure formed by a molecular machine of the present invention. Additional applications will be apparent to those of skill in the art upon consideration of the present disclosure.

VI.C.2. A Molecular Machine for Forming a Nanoparticle Assembly

Nanotechnology in general and nanoparticle research in particular have recently become an area of intense interest. Nanoparticles (e.g., particles with physical size (diameter) of about 100 nanometers (nm) diameter or less) possess important technological properties ranging from superior mechanical behavior to novel electronic and magnetic properties by virtue of their nanocrystalline or other nanoscale microstructural features.

Nanoparticles can play a role in many applications. One area of interest has been, for example, the use of derivatized nanoparticles in drug delivery. The development of therapeutic nanoparticles was first attempted around 1970, and the proposed nanoparticles were intended to function as carriers of anticancer and other drugs (Couvreur et al., (1982) *J. Pharm. Sci.*, 71: 790–92). Attempts were also made to elucidate methods by which the uptake of the nanoparticles by the cells of the reticuloendothelial system (RES) would be minimized (Couvreur et al., (1986) in *Polymeric Nanoparticles and Microspheres*, (Guiot & Couvreur, eds.), CRC Press, Boca Raton, Fla., United States of America, pp. 27–93). Other attempts pursued the use of nanoparticles for treatment of specific disorders. See, e.g., Labhasetwar et al., (1997) *Adv. Drug. Del. Rev.*, 24: 63–85. Nanoparticle assemblies adapted for drug delivery can be synthesized by a molecular machine of the present invention.

Because of their size (e.g., 1–100 nm) nanoparticles exhibit surface and volume effects not observed for larger dimension particles. As a result, nanoparticles can have unique optical, dielectric, magnetic, mechanical, and transport properties that can be employed in many types of applications such as sensors, optics, ceramics, and metallurgy. The synthesis and characterization of nanoparticles has also received attention in recent years for their use as catalysts. Nanoparticles can also be employed as toner in xerography, in ferrofluid vacuum seals, in nuclear magnetic resonance imaging as contrast agents, and in magnetic data storage. A molecular machine of the present invention can be employed to form nanoparticle assemblies that can be employed in these and other applications.

Figure 8:
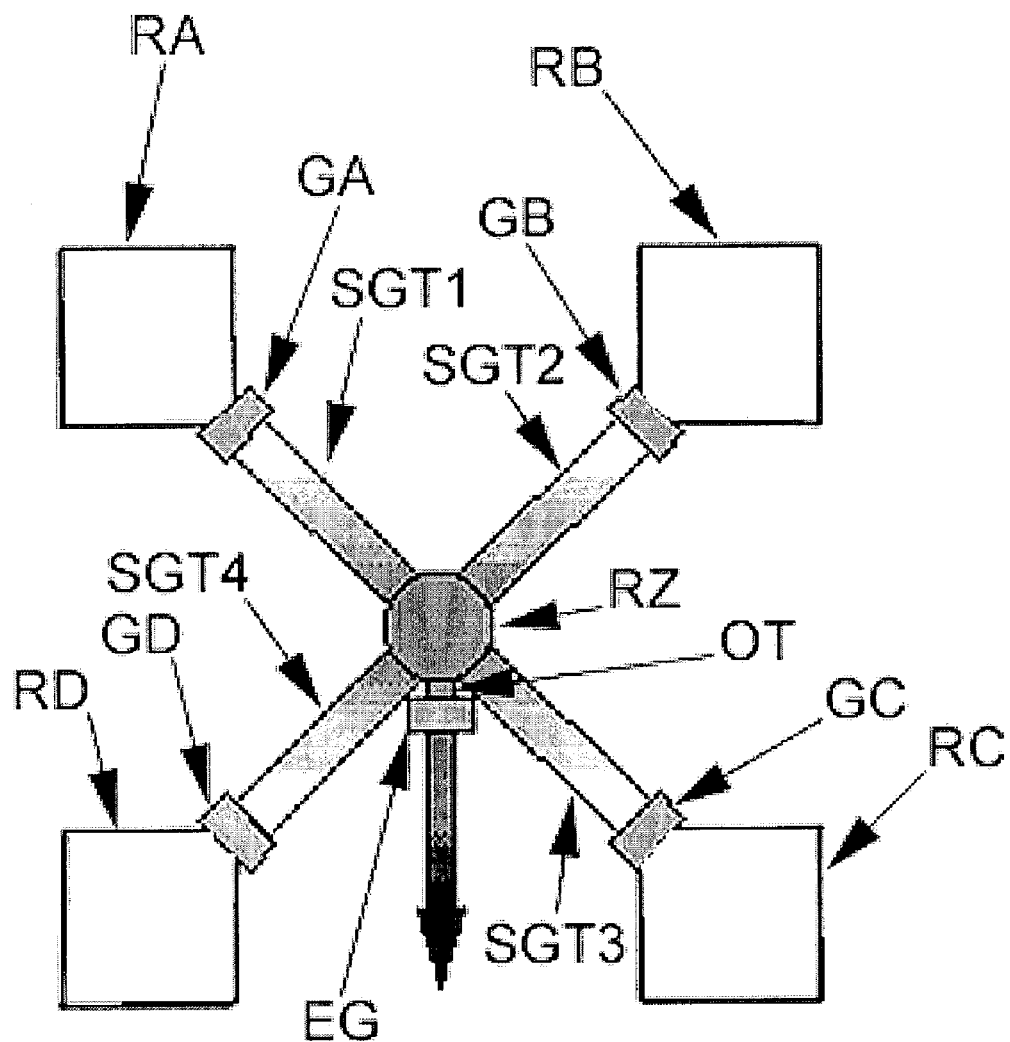
FIG. 8 is a schematic diagram depicting an embodiment of a molecular machine adapted to assemble a particle or molecule.

Synthesis of chemically diverse particles of arbitrary, but predefined, composition and size is currently not possible. However, a molecular machine comprising gradients, independently operable gates, and a central reactor zone (such as the arrangement disclosed in FIG. 8), can facilitate the rapid synthesis of such structures. Referring to FIG. 8, the molecular machine depicted in this figure comprises four gated reservoirs RA, RB, RC, and RD that can release particles into four different gradients. After release, the particles migrate into a reactor zone RZ, each under the influence of an independent gradient. When they reach reactor zone RZ, association of the particles with each other or even modification of the particles can be performed. For example, reservoir RA can comprise a reaction component to be associated with a nanoparticle. Reservoir RB can comprise the nanoparticle. This association can be performed in reactor zone RZ, once each component is present in reactor zone RZ. This association can be assisted or initiated by the application of an external stimulus. Assembly can be driven photochemically, for example, through the use of particles with photochemically-active surface chemistries. Following reaction, the nanoparticle assemblies can be released out of reactor zone RZ through an exit gate EG into a gradient via application of a driving force, and the cycle can begin anew.

Continuing with FIG. 8, a molecular machine MM for assembling a nanoparticle assembly comprises two or more reservoirs RA, RB, RC, and RD comprising reaction components. Reaction components can comprise chemical moieties and/or nanoparticles. For example, reservoir RB can comprise a nanoparticle that is to be derivatized with one or more chemical moieties. Reservoirs RA, RB, RC, and RD can comprise the chemical moieties that are to be associated with the nanoparticle. Broadly, a reservoir RA, RB, RC, or RD can comprise any chemical or nanoparticle structure. Preferably, reservoir RA, RB, RC, or RD comprises an area of high driving force. Even more preferably, reservoir RA, RB, RC, or RD comprises an area having the strongest driving force associated with molecular machine MM.

Continuing with FIG. 8, a molecular machine MM can optionally further comprises two or more independently operable gate structures GA, GB, GC, and GD in communication with two or more reservoirs RA, RB, RC, and RD of components. As disclosed herein above, a gate structure can function by any theory of operation. For example, a gate can operate based on a physical conformation that sterically inhibits flow of a reaction component out of a reservoir. Alternatively, a gate structure also can function by an electrostatic theory of operation. A given gate structure can also be adapted to respond independently from any other gate structure. In one embodiment, a gate structure can be opened or closed without regard to the open or closed status of other gates comprising the molecular machine.

Next, molecular machine MM preferably comprises two or more static gradient tracks SGT1, SGT2, SGT3, and SGT4, each static gradient track SGT1, SGT2, SGT3, and SGT4 communicating with one of the two or more independently operable gate structures GA, GB, GC, and GD, respectively and reactor zone RZ, the two or more static gradient tracks comprising fixed regions of high and low driving force. The static gradient tracks SGT1, SGT2, SGT3, and SGT4 can be formed as disclosed herein. By virtue of the fact that the gradients are static, they are adapted to transport a molecule or particle in only one direction. In one embodiment, molecular machine MM is configured such that a region of high driving force of a static gradient is situated in communication with a gate, which itself communicates with a reservoir. In one embodiment, a region of low driving force is disposed in communication with reactor zone RZ. In FIG. 8, darker shading indicates regions of low driving force and lighter shading represents regions of high driving force.

Continuing with FIG. 8, reactor zone RZ can comprise an area of driving force that is lower than the area of low driving force associated with a static gradient. This configuration facilitates the transport down the static gradient to reactor zone RZ. Thus, reactor zone RZ can comprise an area of driving force lower than those associated with a static gradient. Reactor zone RZ can serve as the site for nanoparticle assembly. The term "nanoparticle assembly" is used in its broadest sense and encompasses not only association of two or more nanoparticles, but the association of one or more chemical moieties with one or more nanoparticles as well.

Continuing with FIG. 8, molecular machine MM also can comprise an output track OT, which comprises a static gradient directing an assembled nanoparticle assembly away from reactor zone RZ. In one embodiment, output track OT comprises a static gradient that is lower in driving force than the driving force associated with reactor zone RZ. In this configuration, a nanoparticle assembly that has been assembled (or derivatized) is directed out of the area of reactor zone RZ by virtue of the path of decreasing driving force. In one embodiment, molecular machine MM comprises an independently operable gate structure EG in communication with output track OT and reactor zone RZ. This gate structure EG preferably follows that same theory of operation disclosed herein and is of a similar configuration.

In operation, a molecular machine can function to assemble or derivatize a nanoparticle-based structure. Referring again to FIG. 8, a general sequence of operation can proceed as follows. Initially, a nanoparticle is released from a reservoir, e.g. reservoir RB. When the particle is released from reservoir RB, a step in the process is the triggering of gate structure GB. Triggering gate structure GB releases a particle from the high driving force region RB. The particle follows the driving force gradient path down the gradient to reactor zone RZ. Subsequently, a second gate structure is triggered, e.g. gate GA, thereby releasing a particle or chemical moiety from a second reservoir, e.g. reservoir RA. The particle or chemical moiety then follows the gradient away from the region of higher driving force to a region of lower driving force, e.g. to reactor zone RZ. Upon entering reactor zone RZ, the two elements are associated with one another. The association can comprise a covalent, non-covalent, or ionic association. Depending on the nature of the association, the conditions of reactor zone RZ (which in one embodiment are variable) can be conducive to the nature of the association to be performed.

Continuing with FIG. 8, these steps can be repeated a desired number of times until all desired reservoir components are associated with a nanoparticle assembly which, to this point, is maintained in reactor zone RZ. When all association reactions are completed, gate structure EG, which is in communication with reactor zone RZ, is triggered to release the nanoparticle assembly from reactor zone RZ. An output track OT comprising a gradient, which itself comprises a region of driving force lower than that of reactor zone RZ, then transports the particle away from reactor zone RZ. Gate structures GA, GB, GC, and GD can then be reset as required and the process can start again.

Figure 9:
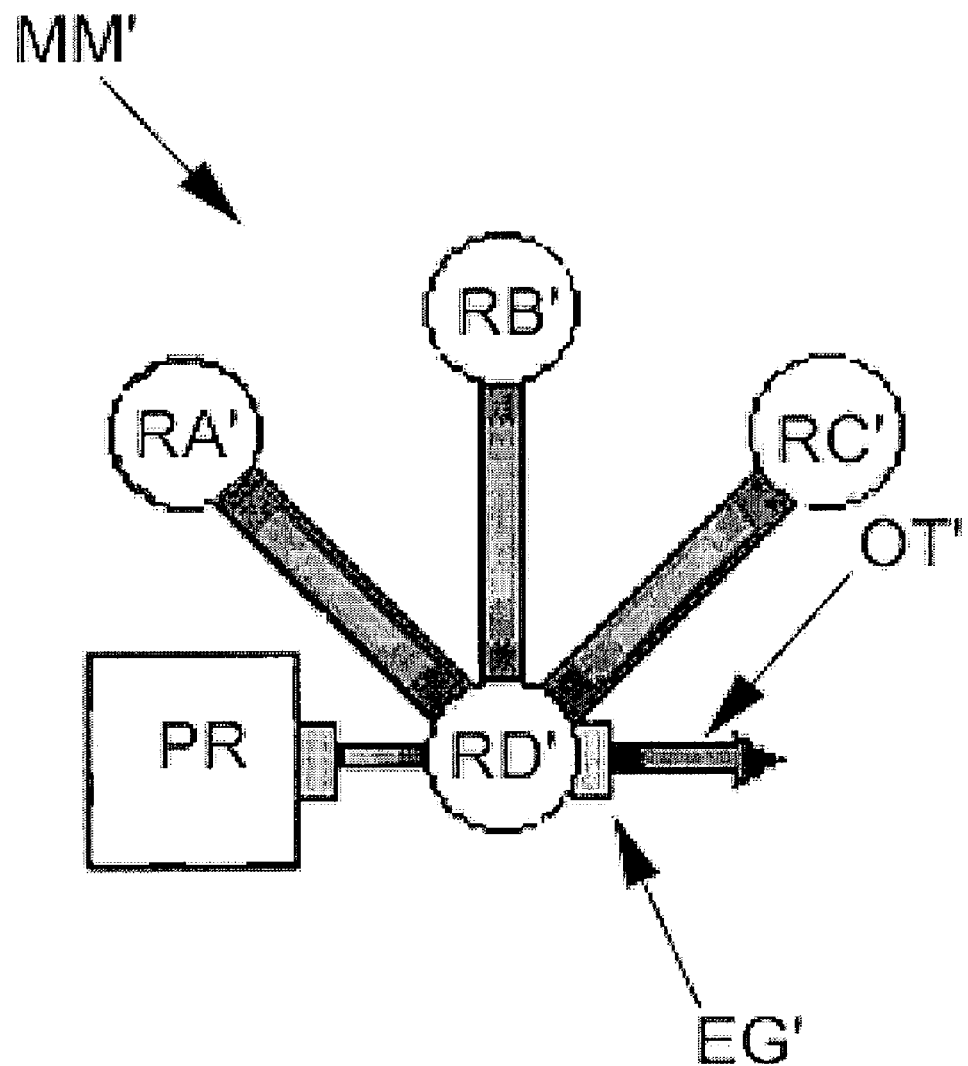
FIG. 9 is a schematic diagram depicting an embodiment of a molecular machine adapted to assemble a particle or molecule.

VI.C.3. Molecular Machine for Synthesizing a Nanoparticle Heterostructure of Arbitrary Sequence A molecular machine comprising a dynamic gradient can yield a complex product, which often cannot be manufactured by another approach. In one embodiment, depicted in FIG. 9, molecular machine MM' can move individual nanoparticles between the four reservoirs RA', RB', RC', and RD' depicted. In this embodiment, each reservoir RA', RB', RC', and RD' can be designed to carry out a specific chemical reaction to modify the surface of a nanoparticle or a subject molecule. Continuing with FIG. 9, reservoirs RA', RB', and RC' can each comprise a different protected peptide. A nanoparticle enters each respective reservoir RA', RB', and RC' from particle reservoir PR and a peptide is associated with the surface of the nanoparticle. After peptide association, the nanoparticle moves to a deprotection reservoir, RD', whereupon the surface is reactivated for an additional peptide association operation. The nanoparticle then transfers into another peptide reservoir and so on. The final product of molecular machine MM' is a molecule or nanoparticle comprising rigorously defined molecular weight and structure, and is moved along an output track OT' via exit gate EG'. The variable motion of a particle in molecular machine MM' can be controlled via the application of one or more dynamic gradients.

In this molecular machine embodiment, the gradients can be dynamic gradients. By employing dynamic gradients, it is possible to exercise a significant degree of control over the formation of an assembly. For example, by employing dynamic gradients in a molecular machine it is possible to control the rate at which particles are transported to a reactor zone. This level of control can facilitate the rate at which an assembly is formed.

The dynamic gradients of a molecular machine can also be employed to control the order in which an assembly is formed. For example, the dynamic gradients of a molecular machine can be operated so as to release particles and/or components from one or more reservoirs in a particular sequence. The particles and/or components can then move along a gradient to a reactor zone for subsequent association with one another or with an assembly that is partially formed. By employing dynamic gradients to control the order of release from a reservoir, the order in which an assembly is formed can also be controlled.

The molecular machines of the present invention are not limited in application to nanoparticle derivatization, nor are they limited to synthesis of a particular type of molecule, although biomolecules are a representative class of molecules that can be synthesized by employing the molecular machines of the present invention. A full range of organic chemistry reactions can be carried out, yielding a wide range of polymers. Inorganic chemistry reactions are also possible. The concept of automated synthesis of polypeptides or polynucleotides is not new, but presently requires complicated and expensive machinery. The disclosed on-chip synthesis of the present invention facilitates the synthesis of specific compounds in virtually any environment and reduces the need for complex and costly apparatuses. The molecular machines of the present invention offer the added advantage that they can be operated under computer control with only minimal training.

In accordance with the present invention, a molecular machine for synthesizing a structure is disclosed. In one embodiment, the molecular machine comprises a reservoir comprising a starting material. The reservoir can comprise a structure formed in a SAM, as disclosed herein. The structure can comprise any starting material, including, but not limited to chemical moieties and particles, such as nanoparticles.

In one embodiment, an application of this type of molecular machine can comprise the synthesis of a biomolecule, Which includes organic molecules of biological interest. A biomolecule can be synthesized based on a starting material such as an amino acid or a nucleic acid, or it can be synthesized on the surface of a particle. Such particles can be useful for drug delivery, as disclosed herein. In these cases, representative starting materials comprise a particle or a "seed" molecule. When a molecule other than a biomolecule is being synthesized, a starting material can comprise a scaffold upon which the molecule can be built.

Optionally, a molecular machine of the present invention can further comprise two or more dynamic gradient tracks, each in communication with a reaction site, the two or more dynamic gradient tracks comprising regions of variable potential energy and each reaction site comprising a reaction component. The two or more dynamic gradient tracks can be formed as described herein. A characteristic of a dynamic gradient that makes it useful in a molecular machine of the present invention is the ability to change the "direction" of a dynamic gradient by applying a stimulus. By changing the direction of a dynamic gradient, an intermediate structure can be transported from one location to another location by the same dynamic gradient. As noted throughout the present disclosure, a gradient functions to transport a molecule or particle based on the driving force associated with a given gradient at the point at which the particle or molecule is associated with the gradient.

A molecular machine of the present invention can optionally further comprise an output track comprising a dynamic gradient track comprising a region of variable driving force and adapted to direct a completed structure away from a reaction site. A completed structure can be directed away from all reaction sites and out of the machine itself via a dynamic gradient. Additionally, to ensure that a structure that is not yet complete does not leave the machine, an independently operable gate structure in communication With the output track can form a component of the molecular machine. The gate structure can be adapted to open in response to a stimulus and close response to a second stimulus, or in response to the removal of a stimulus. The gate associated with the output track can be operated independent from the gate associated with the reservoir comprising a starting material.

In operation, this type of molecular machine can function generally as follows. Initially, a starting material is provided. A starting material can comprise any material, including, but not limited to biomolecules, such as amino acids and nucleotides, organic molecules, and nanoparticles. Next, the starting material is transported to a reaction site comprising a reaction component. The reaction component can also be any type of material. The choice of a reaction component can be based, in part, on the overall function of the molecular machine. For example, if the molecular machine is designed to form a peptide comprising a certain sequence, a reaction component can comprise a quantity of a given amino acid. Alternatively, if a molecular machine is designed to synthesize a certain nucleotide sequence, a reaction component can comprise a quantity of a given nucleotide. Reaction components can also comprise a quantity of nanoparticles. Summarily, a suitable reaction component can be determined by the overall design and goal of the molecular machine.

Subsequently, a chemical reaction is performed on the starting material, which comprises associating a reaction component with the starting material to form an intermediate structure. Again, the precise nature of the association (e.g., covalent bonding, non-covalent bonding, ionic bonding, etc.) will be determined by the overall function of the molecular machine.

After formation of an intermediate structure, the intermediate structure is then transported to a reaction site distinct from the first reaction site, the distinct site comprising a reaction component. In this way, the same machine can perform multiple rounds of synthesis. The steps of directing an intermediate structure to a new reaction site, performing the reaction, and directing the intermediate structure away from the reaction site can be performed a desired number of times to form a completed structure. Finally, the completed structure is directed down the output track and out of the immediate vicinity of the machine. Alternatively, the output track can lead to a storage facility, which can comprise an element of the machine and/or can be disposed on the same surface as the machine itself.

It is noted that all transportation in the molecular machine is achieved by employing dynamic gradients. The theory of operation of these gradients is described herein above. Generally, the transportation of a molecule or particle can be achieved by altering the direction of the gradient (i.e., changing the orientation of the high-to-low driving force direction of the gradient) so as to direct a structure to a desired location. Gate design and operation can follow the parameters disclosed herein above.

VII. Conclusions

The methods, gradients and molecular machines of the present invention can be employed in a wide range of applications. For example, the present invention can be employed in the fabrication of electronic components and in the synthesis of organic and biomolecules and other structures of interest. Notably, many of the methods of the present invention can involve incorporation and modification of nanoparticles. For example, the present invention can be employed to modify the surface of a nanoparticle, thereby transforming it into a structure useful in a range of applications. For example, nanoparticles can be employed in drug delivery, material science research and applications, and molecular detection and identification applications, to name just a few well-known applications. All of these applications can employ a derivatized nanoparticle formed by the methods and machines of the present invention.

The gradients of the present invention also represent an advance over the prior art. The gradients of the present invention can be easily formed and do not require highly specialized equipment to generate the structures or compounds that form elements of a gradient. The methods of forming a desorbed pattern and substitution of a patterning material for matrix material, an element of some gradients, can be extended to form patterns on structures. The ability to direct molecules in definite patterns by employing gradient structures such as those of the present invention is unprecedented.

Summarily, the methods and structures of the present invention can be employed in a range of applications, from electronics to drug delivery. Moreover, the molecular machines of the present invention, which employ dynamic and static gradients, represent an advance over the prior art. The novel gradients and methods of the present invention make these applications possible.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications, and alterations can be employed without departing from the spirit and scope of the invention.

Laboratory Example 1

Figure 10:
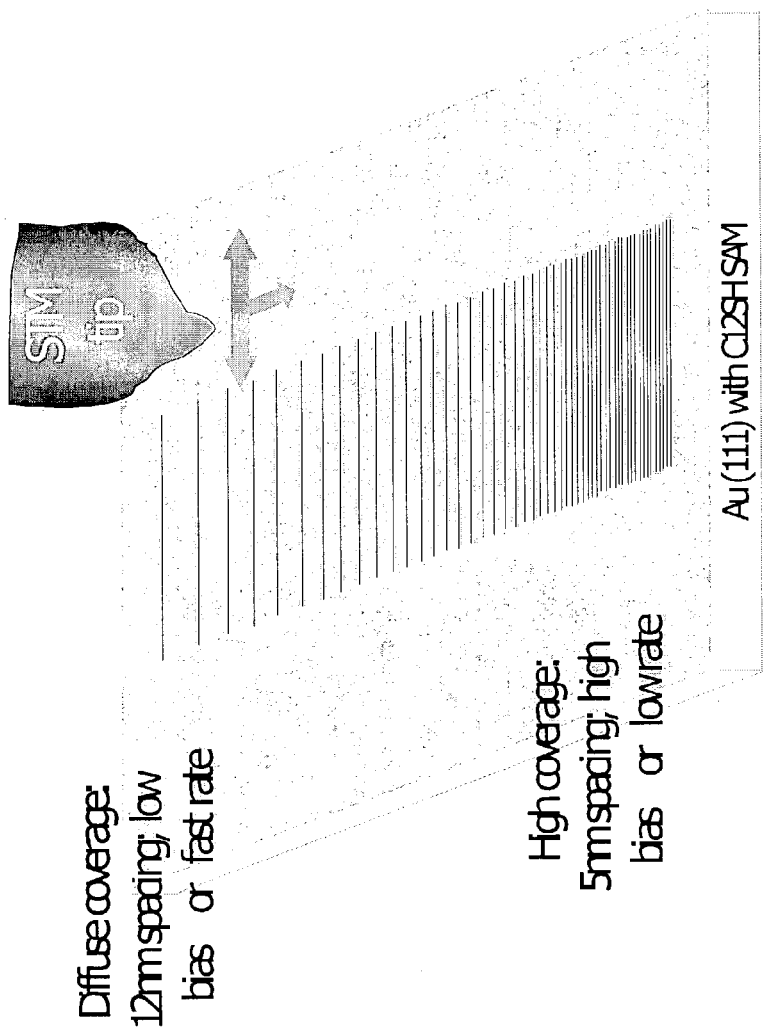
FIG. 10 is a schematic depicting a gradient tip raster pattern.

One embodiment of a line raster pattern that can be employed in the fabrication of a gradient is disclosed. A line spacing of 12 nm is employed to form an area of diffuse coverage and is incrementally decreased in steps of about 2.5 nm to 5 nm to form an area of high coverage (i.e., the areas where desorption of matrix material and substitution of patterning material for matrix material is more complete). Since the average line resolution of this technique is 10 to 15 nm, this generates a gradient in which there is very little overlap of substitution lines in the diffuse coverage area and complete overlap of substitution lines in the high coverage area. This level of detail and resolution can be achieved, in part, due to the plurality of parameters that can be optimized. See FIG. 10.

Laboratory Example 2

Nanostructures were obtained by systematic variation in the replacement bias to promote thiolate desorption. The lithographic pattern contains two rows of six parallel lines, each 200 nm in length, and separated by 100 nm. In this example, the lithographic scan rate (50 nm/s), tunneling set point current (8 pA), and relative humidity (57%) were kept constant, while the replacement bias was incrementally increased as each line was drawn. At low replacement bias (2.6–2.8 V), no substitution of $FcC_{11}SAc$ for $C_{12}S$-SAM, the matrix material, occurred. As the replacement bias was increased, the extent of substitution increased. A bias range of 3.2–3.4 V gave optimal replacement of the $FcC_{11}SAc$ into the background SAM. As the replacement bias was further increased, the efficiency of substitution became less controllable. At higher bias, inconsistent line widths and etching of the Au substrate beneath the monolayer occurred. The latter can be observed by the dark line parallel through the middle of line patterned at 3.7 V.

Figures 11A, 11B:
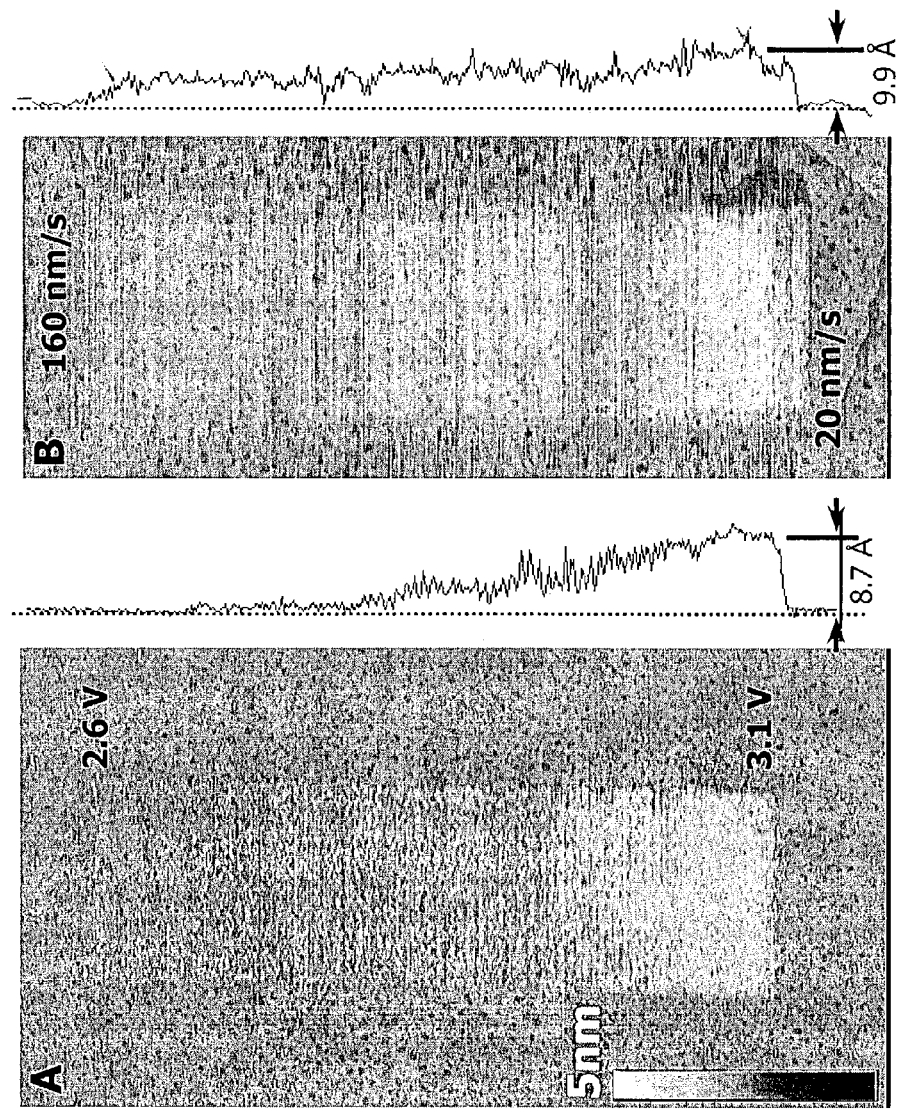
FIG. 11A depicts STM images of $FcC_{11}S$-SAM mesoscale chemical gradients fabricated by systematically varying replacement bias while maintaining all other STM parameters constant. Replacement condition limits are annotated in image. The averaged section analysis is shown to the right of each gradient structure. z-scale: 5 nm.
FIG. 11B depicts STM images of $FcC_{11}S$-SAM mesoscale chemical gradients fabricated by systematically varying lithographic scan rate while maintaining all other STM parameters constant. Replacement condition limits are annotated in image. The averaged section analysis is shown to the right of each gradient structure. z-scale: 5 nm.

The lithographic scan rate also affects the replacement. A pattern was generated that contained two rows of seven parallel lines, each 200 nm in length, and spaced 100 nm apart. In this example, the replacement bias (3.2 V), tunneling set point current (10 pA), and relative humidity (58%) were kept constant. At low scan rate (10 nm/s), complete replacement occurred, however the lines widths were larger than those obtained using a faster scan rate. As the scan rate was increased, rates of 20 to 40 nm/s yielded optimal replacement and ~15 nm line widths. Further increases in scan rate diminished the relative amount of substitution. The patterned lines became blotchy, appearing to leave some of the original $C_{12}S$-SAM matrix material intact within the desired lithographic line pattern. At very high scan rates (>130 nm/s) the substitution of $FcC_{11}SAc$ within the patterned line appeared diffuse. In this example, the tip moved at a high enough scan rate that complete tip-induced substitution is not promoted. See also FIGS. 11A and 11B.

Thus, when performing molecular replacement and/or nanolithography, it is desirable to maintain at least these three parameters at preferred conditions. It is noted however that by varying these three parameters the precise methods and quality of molecular replacement can be varied.

Laboratory Example 3

Figure 12:
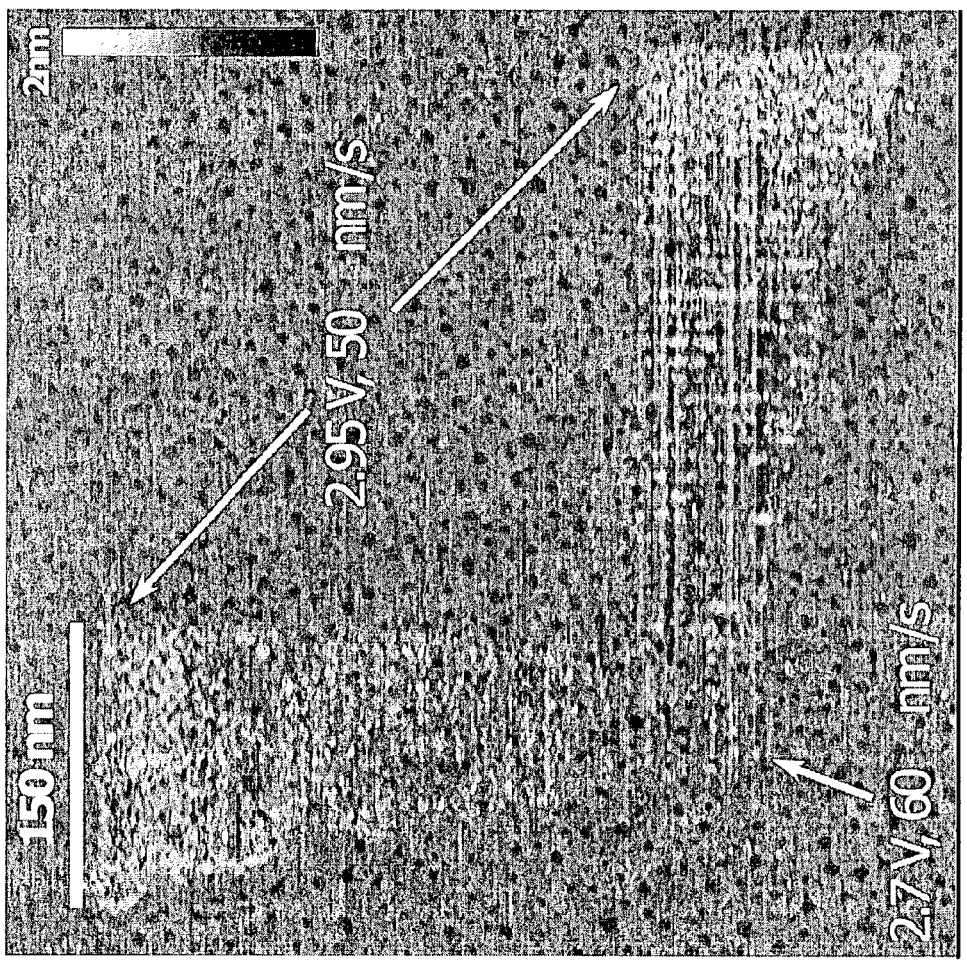
FIG. 12 depicts an STM image of a multidirectional ('L' shape) $FcC_{11}S$-SAM gradient fabricated by systematically varying thiolate replacement conditions as described in the text. Replacement condition limits are annotated in image. z-scale: 4 nm.

A multidirectional gradient structure was fabricated. This gradient structure was fabricated to have high substitution coverage at the ends of the "L" shape, and diffuse coverage in the elbow region. The gradient structure was formed with a constant tunneling setpoint current (10 pA) and relative humidity (58%), but with systematic variation of the replacement bias, the scan rate, the length of lines being substituted, and the raster line spacing within the pattern. As the vertical leg of the "L" was formed, the replacement bias was varied from 2.95 V to 2.7 V, the scan rate was varied from 50 nm/s to 60 nm/s, the line length was varied from 150 nm to 70 nm and the raster line spacing was varied from 4 nm to 11 nm. The scan angle Was then rotated 90 degrees and this process was repeated in reverse to draw the horizontal leg of the "L". This example illustrates the ability to form complex gradient structures by employing the systematic variations described above. These systematic variations in substitution conditions promote a gradual change in chemical heterogeneity between the patterning material and the matrix material over a multidirectional pattern. See FIG. 12.

REFERENCES

The references listed below as well as all references cited in the specification are incorporated herein by reference to the extent that they supplement, explain, provide a background for or teach methodology, techniques and/or compositions employed herein.

Batchelder et al., (1994) *J. Am. Chem. Soc.* 116: 1050–1053
Chaudhury & Whitesides, (1992) *Science* 256: 1539
Couvreur et al., (1982) *J. Pharm. Sci.,* 71: 790–92
Couvreur et al., (1986) in Polymeric Nanoparticles and Microspheres, (Guiot & Couvreur, eds.), pp. 27–93, CRC Press, Boca Raton, Fla., United States of America
Daniel et al., (2001) *Science* 291: 633
Dubois et al., (1992) *Annu. Rev. Phys. Chem.* 43: 437
Enustun & Turkevich, (1963) *J. Am. Chem. Soc.* 85:3317
Gallardo et al., (1999) *Science* 283: 57
Gorman et al., (2000) *Langmuir* 16: 6312
Hayashi, (1987) *J. Vac. Sci. Technol.* A5(4): 1375–84
Hayashi, (1987) *Physics Today*, December 1987, 44–60
Hong et al., (1999) *Science* 286: 523
Kim et al., (1994) *Tetrahedron Lett.* 35(51): 9501–9504
Kim et al., (1995) *J. Am. Chem. Soc.* 117: 3963–3967
Kumar & Whitesides, (1993) *Appl. Phys. Lett.* 63: 2002–2004
Labhasetwar et al., (1997) *Adv. Drug. Del. Rev.,* 24: 63–85
Lestelius et al., (1999) *Colloid Surface B* 15: 57
Liedberg & Tengvall, (1995) *Langmuir* 11: 3821
Liedberg et al., (1997) *Langmuir* 13: 5329
Maoz et al., (1999) *Adv. Mater.* 11: 55
Maoz et al., (2000) *Adv. Mater.* 12: 424
Marinakos et al., (1998) *Chem. Mater.* 10:1214–19
Marinakos et al., (1999) *Adv. Mater.* 11:34
*MRS Bulletin*, January 1990, pgs. 16–47
Piner et al., (1999) *Science* 283: 661
Ross et al, (1993) *Langmuir* 9: 632
Ruardy et al., (1997) *Surf. Sci. Rep.* 29: 1
Schoer et al., (1996) *J. Phys. Chem.* 100:11086
Shedd et al., (1990) *Nanotechnology* 1: 67–80
Tao, (1996) *Phys. Rev. Lett.* 76: 4066
Terrill et al., (2000) *J. Am. Chem. Soc.* 122: 988
Weiss et al., (1996) *Ann. NY Acad. Sci.* 852: 145
Xu & Liu, (1997) *Langmuir* 13: 127
Xu et al., (1998) *J. Am. Chem. Soc.* 120: 9356
Xu et al., (1999) *Langmuir* 15: 7244
Zamborini & Crooks, (1998) *J. Am. Chem. Soc.* 120: 9700
U.S. Pat. No. 4,198,644

It will be understood that various details of the invention may be changed without departing from the scope of the invention. Furthermore, the foregoing description is for the purpose of illustration only, and not for the purpose of limitation—the invention being defined by the claims.

What is claimed is:

1. A dynamic gradient adapted to transport a fluid or a non-fluid, the dynamic gradient comprising:
   (a) a surface;
   (b) a self-assembled monolayer (SAM) disposed on the surface, the SAM comprising a patterning material which comprises at least a portion of head groups whose chemical structure can vary in response to a stimulus applied to the gradient, such that the variation in structure will alter a degree, direction, or both a degree or direction of a driving force of the gradient; and (c) a stimulus.

2. The gradient of claim 1, wherein the surface is selected from the group consisting of gold, silver, copper, nickel, platinum, palladium, indium tin oxide, yttrium-barium-copper oxide, conducting metal oxides, electroactive materials and conducting materials.

3. The gradient of claim 1, wherein the patterning material comprises a binding group and a head group.

4. The gradient of claim 3, wherein the binding group is selected from the group consisting of thiolates, isocyanides, carboxylic acids, sulfonic acids, phosphonic acids, hydroxamic acids, alcohols, amines, monochlorosilanes, dichlorosilanes, trichlorosilanes, monoalkoxysilanes, dialkoxysilanes, and trialkoxysilanes.

5. The gradient of claim 3 wherein the head group is selected from the group consisting of a hydrophobic moiety, a hydrophilic moiety, a photoactive moiety, an acidic moiety, a basic moiety, a moiety with a known binding affinity for another molecule, and an electroactive moiety.

6. The gradient of claim 1, wherein the SAM comprises a matrix material, which comprises a binding group and a head group.

7. The gradient of claim 6, wherein the binding group is selected from the group consisting of thiolates, isocyanides, carboxylic acids, sulfonic acids, phosphonic acids, hydroxamic acids, alcohols, amines, monochlorosilanes, dichlorosilanes, trichlorosilanes, monoalkoxysilanes, dialkoxysilanes, and trialkoxysilanes.

8. The gradient of claim 6 wherein the head group is selected from the group consisting of a hydrophobic moiety, a hydrophilic moiety, a photoactive moiety, an acidic moiety, a basic moiety, a moiety with a known binding affinity for another molecule, and an electroactive moiety.

9. The gradient of claim 1, wherein the stimulus is selected from the group consisting of a change in pH, application of an electric current, and presence of a chemical that can cause a transient chemical modification to a head group.

10. The gradient of claim 1, wherein the variation in structure is selected from the group of transformations consisting of ionization, protonation, a redox reaction, transient chemical modification to form a more hydrophilic structure, and transient chemical modification to form a more hydrophobic structure.

11. The gradient of claim 6, wherein at least a portion of the head groups of the matrix material can vary in chemical structure in response to a stimulus applied to the gradient, such that the variation in stwcture will alter a degree, direction, or both a degree or direction of a driving force of the gradient.

* * * * *